United States Patent
Wallace et al.

(10) Patent No.: US 6,495,127 B1
(45) Date of Patent: Dec. 17, 2002

(54) COMPOSITIONS AND SYSTEMS FOR FORMING HIGH STRENGTH MEDICAL SEALANTS, AND ASSOCIATED METHODS OF PREPARATION AND USE

(75) Inventors: Donald G. Wallace, Menlo Park; George H. Chu, Cupertino; Jacqueline Anne Schroeder, Boulder Creek, all of CA (US)

(73) Assignee: Cohesion Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/649,337

(22) Filed: Aug. 28, 2000

Related U.S. Application Data

(60) Provisional application No. 60/151,273, filed on Aug. 27, 1999.

(51) Int. Cl.⁷ ............... A61K 31/74; A61K 9/14; A61F 13/00; A61F 2/00; A61L 15/00
(52) U.S. Cl. ............... 424/78.03; 424/78.02; 424/422; 424/423; 424/424; 424/443; 424/445; 424/486
(58) Field of Search ............... 424/78.03, 422, 424/78.02, 443, 445, 486, 423, 424

(56) References Cited

U.S. PATENT DOCUMENTS 4,695,602 A 9/1987 Crosby et al.
5,643,575 A 7/1997 Martinez et al.
5,681,904 A 10/1997 Manzara

FOREIGN PATENT DOCUMENTS

WO WO 97/22371 6/1997
WO WO-97/22371 * 6/1997

OTHER PUBLICATIONS

Kroschwiz (1990), *Concise Encyclopedia of Polymer Science and Engineering*, Wiley Intersciences Edition, New York, NY, p. 489.

* cited by examiner

*Primary Examiner*—Thurman K. Page
*Assistant Examiner*—Blessing Fubara
(74) *Attorney, Agent, or Firm*—Dianne E. Reed; Reed & Associates

(57) ABSTRACT

The present invention relates generally to synthetic polymer compositions that form interpenetrating polymer networks. In a preferred embodiment, the compositions comprise two multifunctionally activated synthetic polymers, along with a tensile strength enhancer. Such compositions form matrices that exhibit superior cohesive strength and in many instances can serve as adequate replacements for surgical means of attaching tissues, such as sutures and medical staples.

81 Claims, 18 Drawing Sheets

Penta-erythritol Tetrakis(trimercapto propionate) (PESH-P)

Penta-erythritol tetraacrylate (PETA)

Poly-oxypropylene triamine

Bond Structure Formed Between PESH-P and PETA

Poly(tetramethylene oxide) diamine

Poly(propylene oxide) diacrylate

Poly(propylene oxide) diamine

Scheme 1
continued repeating polymer chain

↓ hydrolysis

↓ re-derivatize with glutaric anhydride and NHS repeating chain with degradable elements (PCL),
reactive pendant groups (NHS), and
water-soluble segments (PEG)

Scheme 2
continued

HO-[PMMA]$_x$-[PEG]$_m$-[PMMA]$_x$-OH

↓ glutaric anhydride

↓ NHS

NHS-glut-[PMMA]$_x$-[PEG]$_m$-[PMMA]$_x$-glut-NHS

↓ lysine following Scheme 1    ↓ hydrolysis

↓ convert pendant COOH to NHS

...[PEG]-[PMMA]$_x$-lys-[PEG]$_m$-[PMMA]$_x$-lys-[PMMA]$_x$-[PEG]...
                                NHS                      NHS or ...[PMMA]$_x$-lys-[PMMA]$_x$-[PCL]$_m$-[PEG]$_n$-[PCL]$_m$-[PMMA]$_x$-lys-[PMMA]$_x$...
             NHS                                                NHS

FIG. 8b

COH102: Tetra-Functional Glutaryl-Succinimidyl Polyethylene Glycol

Collagen Membranes

Porcine Carotid Artery

Cowhide Strip

HEMA
hydroxyethyl methacrylate

MMA
methyl methacrylate mono-2-(acryloxy)ethyl succinate 2-aminoethyl methacrylate

COMPOSITIONS AND SYSTEMS FOR FORMING HIGH STRENGTH MEDICAL SEALANTS, AND ASSOCIATED METHODS OF PREPARATION AND USE

CROSS REFERENCE TO RELATED APPLICATIONS

This application claims priority to U.S. Ser. No. 60/151,273, filed on Aug. 27, 1999.

FIELD OF THE INVENTION

This invention relates generally to synthetic polymer compositions that form interpenetrating polymer networks when administered to tissues. Such compositions are particularly well suited for use in a variety of medical applications when the physical strength of the administered material is important. For example, the compositions of the present invention that are designed to be used to attach tissues together are strong enough to provide an effective substitute for other surgical means of attachment, such as sutures and medical staples.

BACKGROUND OF THE INVENTION

The use of polymer compositions in tissue engineering is now widely recognized, particularly those consisting of synthetic polymers. In contrast to many naturally derived compositions, synthetic polymer compositions can be formulated to exhibit predetermined physical characteristics such as gel strength, as well as biological characteristics such as degradability.

In a variety of tissue engineering applications, it is desirable to use compositions that can be administered as liquids, but subsequently form hydrogels at the site of administration. Such in situ hydrogel forming compositions are more convenient to use since they can be administered as liquids from a variety of different devices, and are more adaptable for administration to any site, since they are not preformed. Many different mechanisms have been described that can be used to promote hydrogel formation in situ. For example, photoactivatable mixtures of water-soluble co-polyester prepolymers and polyethylene glycol have been described to create hydrogel barriers, as well as drug release matrices. In another approach, block copolymers of Pluronic and Poloxamer have been designed that are soluble in cold water, but form insoluble hydrogels that adhere to tissues at body temperature (Leach, et al., Am. J. Obstet. Gynecol. 162:1317–1319 (1990)). Polymerizable cyanoacrylates have also been described for use as tissue adhesives (Ellis, et al., J. Otolaryngol. 19:68–72 (1990)). In yet another approach, two-part synthetic polymer compositions have been described that, when mixed together, form covalent bonds with one another, as well as with exposed tissue surfaces (PCT WO 97/22371) In a similar approach involving a two-part composition, a mixture of protein and a bifunctional crosslinking agent has been described for use as a tissue adhesive (U.S. Pat. No. 5,583,114.)

In other tissue engineering applications, it is not necessary or desired for the compositions to be in liquid form when administered. In fact, it may be advantageous in some circumstances to apply compositions that are gelatinous, paste-like, or even preformed solid implants, since these forms tend to stay in place after administration more readily than liquid formulations.

For many tissue engineering applications, it is important that the compositions be capable of forming a matrix after administration that is strong enough to withstand the biological and physical forces to which it will be subjected for a long enough period of time to fulfill its intended purpose. Strength is particularly important when the compositions are used as a partial or total replacement for sutures. In addition, for applications in which adherence to tissues is important, it is necessary for the formulations to have adequate adhesive strength. Cyanoacrylate is a highly effective adhesive that forms a strong matrix, but is too toxic to be used internally and is thus not approved for such uses. Accordingly, it is an object of the present invention to provide compositions that form high strength medical sealants that are not toxic.

SUMMARY OF THE INVENTION

The present invention relates to multifunctional polymer-containing compositions that are specifically designed to exhibit superior strength for one embodiment. The compositions comprise a first multifunctional synthetic polymer having m functional groups, X; a multifunctional crosslinking agent having n functional groups, Y; and a tensile strength enhancer, such that when all three components are mixed together, X and Y react to form a covalently bonded three-dimensional interpenetrating polymer network. In addition, the tensile strength enhancer may become covalently bonded in the network, or it may become physically entrapped therein.

In a preferred embodiment of the present invention, the multifunctional crosslinking agent is a second multifunctional synthetic polymer.

An aspect of the present invention is inclusion of the tensile strength enhancer, which can be comprised of a variety of compounds capable of forming a structure with the appropriate characteristics as described elsewhere herein. Such compounds include, inter alia, Vicryl, glass wool, plastics, resins, and fibers.

The functional groups, X and Y can be any pair of reactive moieties that form a covalent bond, Z, under the appropriate conditions, such as sulfhydryl, succinimidyl, acrilate and amino, which form, in no particular order, ether, ester or disulfide.

In order to enhance or discourage biodegradation of the interpenetrating polymer network, the synthetic polymer core may additional comprise a chain extender. For example, alpha-hydroxy acid, poly(lactone), poly(orthocarbonate) and poly(phosphoester) moieties may serve to enhance biodegradability. In addition, the chain extender may be an enzyme substrate.

In another aspect of the present invention, the composition further comprises optional components, such as proteins, antibiotics, growth factors and hemostatic agents.

In a preferred embodiment of the invention, the optional component is present in the form of a rigid nanofiber, such as that formed by methylated collagen.

In yet another aspect of the invention, X and Y are each 4 or greater to provide for more efficient crosslinking.

In one embodiment, the composition of the present invention comprises a pair of reactive polyalkylene oxides, a rigid nanofiber, such as methylated collagen, and a tensile strength enhancer.

Other aspects of the present invention are described elsewhere herein.

DETAILED DESCRIPTION OF THE INVENTION

Figure 1:
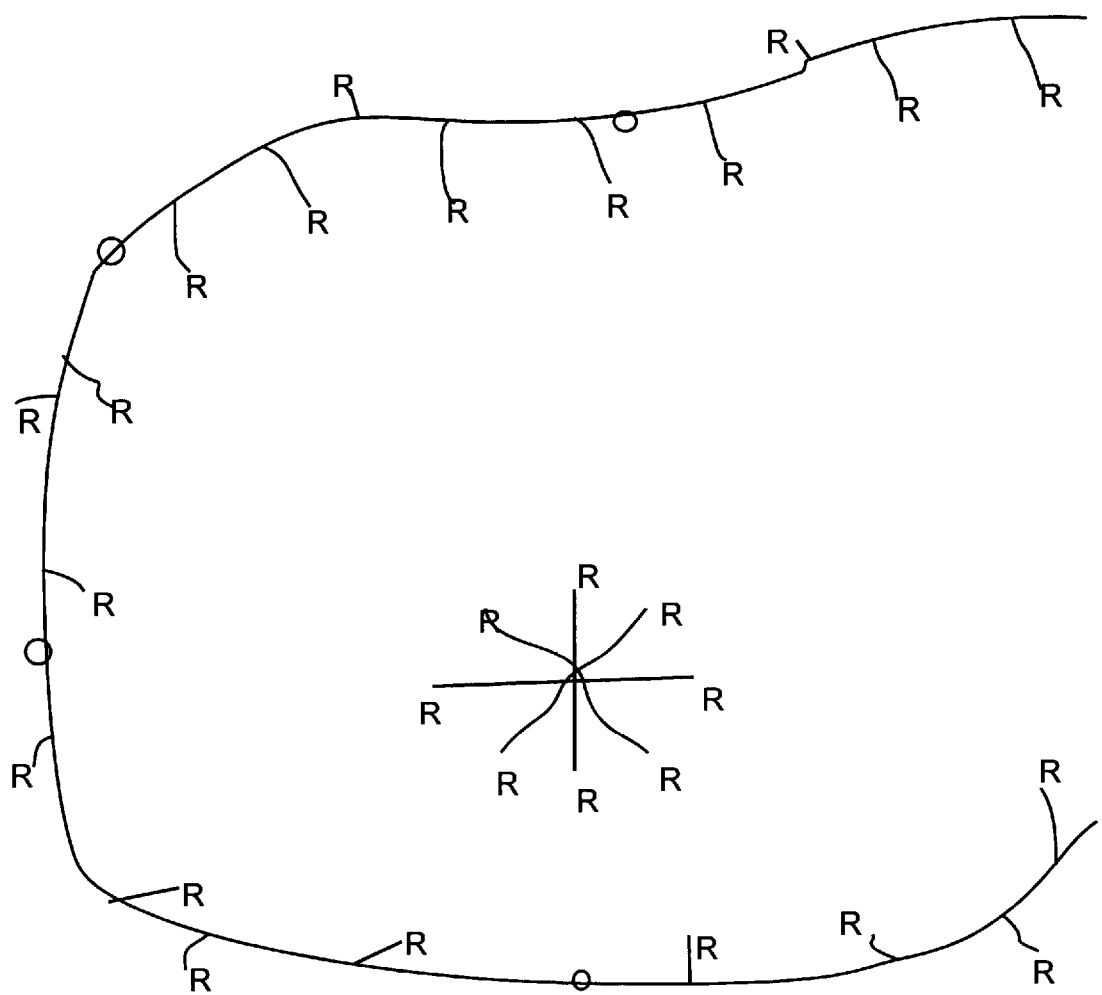
FIG. 1 depicts the structure of linear and branched polymers with biodegradable linkages ("O") and functional groups ("R") attached thereto.

The present invention relates to synthetic polymer compositions that according to one embodiment, form an interpenetrating polymer network when administered to a tissue site. Within a short time (less than 3 minutes) after being administered, the composition forms a network which develops with high cohesive ("tensile") strength, which contemplates that the matrix has a tensile strength of at least 10% and more preferably 20% of that of cyanoacrylate. In a preferred embodiment, such networks exhibit a tensile strength of greater than 60 N/cm². The preferred compositions are designed to become anchored in place by mechanical and/or chemical means to seal tissues together that have become separated as a result of various disease states or surgical procedures. Accordingly, compositions that form networks with adhesive strengths >50 mm Hg (i.e. The burst pressure required to detach the adhesive and create a leak) are preferred for applications when strong tissue adhesion is desired.

In another embodiment, the present invention relates to preformed matrices in the form of dried sheets that can be applied more quickly than a sprayed liquid (for open surgery). The attainment of very high burst strengths at short times (30 sec) may also permit use of active sheets in sites that must be challenged soon after application (30 sec. versus 3 min.).

In yet another embodiment, the present invention comprises activated collagen sponges and sheets as further described in Examples 4 and 5 below.

Defintions

The following definitions are provided to further describe various aspects of the preferred embodiments of the present invention.

The term "gel" refers to the state of matter between liquid and solid. As such, a "gel" has some of the properties of a liquid (i.e., the shape is resilient and deformable) and some of the properties of a solid (i.e., the shape is discrete enough to maintain three dimensions on a two dimensional surface.) Accordingly, "gelation time", also referred to herein as "gel time", refers to the time it takes for a composition to become non-flowable under modest stress. This is generally exhibited as achieving a gel strength, expressed as elastic modulus, G', of greater than or equal to $10^2$ dynes/cm² in less than 1 minute.

The term "cohesive strength" refers to the ability of the compositions of the present invention to remain intact, i.e., not rupture, tear or crack, when subjected to physical stresses or environmental conditions. Cohesive strength is measured herein as a function of "tensile strength".

The term "adhesive strength" refers to the ability of the compositions of the present invention to be able to remain attached to the tissues at the site of administration when subjected to physical stresses or environmental conditions.

The term "polymer" refers to a molecule consisting of individual chemical moieties, which may be the same or different, but are preferably the same, that are joined together. As used herein, the term "polymer" refers to individual chemical moieties that are joined end-to-end to form a linear molecule, as well as individual chemical moieties joined together in the form of a branched (e.g., a "multi-arm" or "star-shaped") structure.

The term "biocompatible" refers to the ability of the compositions of the present invention to be applied to tissues without eliciting significant inflammation and fibrosis or other adverse tissue responses.

The term "synthetic polymer" refers to polymers that are not naturally occurring and that are produced by chemical or recombinant synthesis. As such, naturally occurring proteins such as collagen and naturally occurring polysaccharides such as hyaluronic acid are specifically excluded. Proteins such as synthetic collagen, and carbohydrates such as synthetic hyaluronic acid, and their derivatives, are included.

The term "activated synthetic polymers" refers to synthetic polymers that have or have been chemically modified to have at least one functional group (e.g., a sulfhydryl group) that is capable of reacting with a corresponding reaction partner (e.g., a sulfhydryl-reactive group) to form a covalent bond. The term "multifunctionally activated", or "multifunctional", refers to synthetic polymers having two or more functional (usually nucleophilic or electrophilic) groups. Types of multifunctionally activated synthetic polymers include di-functionally activated, tri-functionally activated, tetra-functionally activated, and star-shaped activated polymers (that have four or more functional groups).

The term "medical sealant" refers to compositions that become anchored in place by mechanical and/or chemical means to seal tissues together that have become separated as the result of various disease states or surgical procedures. For example, medical sealants can be used to fill voids in hard tissues, to join vascular and other soft tissues together, to provide a mechanical barrier to promote hemostasis, and to prevent tissue adhesions by keeping one tissue surface from coming in contact with and becoming adhered to another tissue surface.

The term "interpenetrating polymer network" ("IPN") is intended to describe the matrix that is formed from a reactive polymer or polymers such as PEG, or monomers that are polymerized, which exhibits an infinite molecular weight and includes a co-reactant of a different type, such as a high tensile strength fiber, that interpenetrates within the PEG polymer network to form two continuous networks throughout the network. See Sperling, L.H. et al., "Morphology and Mechanical Behavior of Interpenetrating Polymer Networks", in Polymer Networks, A. J. Chompff and S. Newman, ed., Plenum Press, New York, N.Y. (1971), pages 435–449.

The term "filler" is used to refer to bulking agents, small organic compounds, polymers, fibers, resins, and the like, that are added to chemical compositions for a variety of reasons, the most pertinent to the present invention being to enhance tensile strength.

Composition Components

The compositions of the present invention comprise at least one multi-functional synthetic polymer that, along with a tensile strength enhancer and other optional composition constituents, can form a high strength matrix at the site of administration. The polymeric component provides for a "continuous gel phase" via interconnecting of the flexible polymer when the polymer is crosslinked to other polymers and/or other composition components.

When the compositions comprise a single multi-functional synthetic polymer, they are designed such that the polymer remains in the unreactive state until administered. When the compositions comprise two or more multi-functional synthetic polymers, they are generally designed as two-part compositions that react with one another when mixed at the site of administration. Alternatively, such two-component compositions can also be prepared in an unreactive state and later activated prior to, during or after administration. Additionally, two-part compositions comprising a single synthetic polymer species and a small (i.e. less than half the size of the polymer) crosslinking agent can be utilized. These and other composition formats are described below in more detail.

In a preferred embodiment, the compositions are two-part compositions, each of which comprises a different multi-functionally activated synthetic polymer, such that the polymers will react with one another at the site of administration to form an IPN. As such, they can easily be administered separately.

Such compositions can be generally represented by Formula I as follows:

$$\text{Compound}_1\text{-}X_m + \text{Compound}_2\text{-}Y_n \rightarrow \text{Compound}_1\text{-}Z\text{-}\text{Compound}_2 \quad (I)$$

Compound$_1$ has multiple (m≧2) functional groups (X) that react with Compound$_2$, which has multiple (n≧2) functional groups (Y), such that when functional groups X and Y come in contact under appropriate conditions, covalent bond Z is formed. Accordingly, functional groups X and Y can also be referred to as "reaction partners" of one another and can collectively be referred to as a "reaction pair". As depicted in Formula I for illustration purposes only, there is only one bond formed between Compound$_1$ and Compound$_2$. However, when m+n≧5, and appropriate ratios of the two components are utilized as described elsewhere herein, the two compounds form multiple attachments to one another resulting in a three-dimensional polymer matrix. Preferably, both compounds contain four or more functional groups, since such multifunctionality results in a gel matrix with greater overall cohesive strength. In a particularly preferred embodiment, each of the compounds is tetrafunctionally activated.

In another preferred embodiment, the compounds each have 12 functional groups. Such compounds are formed from reacting a first tetrafunctionally activated polymer with a second tetrafunctionally activated polymer, wherein the functional groups of each of the two compounds are a reaction pair, and react together to form "12-arm" functionally activated polymers. An example of such a "12-arm" compound is dodeca-sulfhydryl-PEG, 50,000 mol. wt., which is constructed from a core tetra-functional succinimide ester PEG coupled to four (exterior) tetra-functional sulfhydryl-PEG molecules. Such polymers range in size from over 10,000 mol. wt. to greater than 100,000 mol. wt. depending on the molecular weight of the tetra-functionally activated polymer starting materials.

Other types of multifunctional polymers can easily be synthesized using routine synthesis. However, care should be taken to produce multi-arm products with consistent arm lengths to avoid steric hindrance of the functional groups. Accordingly, activated polymers that are suitable for use in the present invention may have a variety of geometric shapes and configurations.

Polymer Core

As described above, each of the compounds has multiple functional groups, X and Y. The non-reactive remainder of the compound is considered to be its "core". At least one of the two compounds should have a polymer core in order to form a strong gel matrix. When one of the compounds contains a polymer core, the other compound can be a small organic molecule with multiple functional groups. However, for most applications, it is preferred for both compounds to have the same or a different polymer core.

The polymer core may be a synthetic polyamino acid, a polysaccharide, or a synthetic polymer. For some applications, the preferred polymer core material is a synthetic hydrophilic polymer. Suitable synthetic hydrophilic polymers include, inter alia, polyalkylene oxide, such as polyethylene oxide (($CH_2CH_2O)_n$), polypropylene oxide (($CH(CH_3)CH_2O)_n$) or a polyethylene/polypropylene oxide mixture (($CH_2CH_2O)_n$—($CH(CH_3)CH_2O)_n$). A particularly preferred synthetic hydrophilic polymer for certain applications is a polyethylene glycol (PEG) having a molecular weight within the range of about 100 to about 100,000 mol. wt., more preferably about 1,000 to about 20,000 mol. wt.

More preferably still, when the polymer core is polyethylene glycol, it generally has a molecular weight within the range of about 7,500 to about 20,000 mol. wt. Most preferably, the polyethylene glycol has a molecular weight of approximately 10,000 mol. wt.

Multifunctionally activated polyalkylene oxides, such as polyethylene glycol, are commercially available, and are also easily prepared using known methods. For example, see Chapter 22 of Poly(ethylene Glycol) Chemistry: Biotechnical and Biomedical Applications, J. Milton Harris, ed., Plenum Press, NY (1992); and Shearwater Polymers, Inc. Catalog, Polyethylene Glycol Derivatives, Huntsville, Alabama (1997–1998). For use as a tissue sealant, the exemplary combination of activated polymers is as follows: tetrafunctionally PEG, pentaerythritol poly(ethylene glycol) ether tetra-succinimidyl glutarate (10,000 mol. wt.); and tetrafunctional PEG, pentaerythritol poly(ethylene glycol) ether tetra-sulfhydryl (10,000 mol. wt.). In both cases, these "four-arm" PEGs are formed by ethoxylation of pentaerythritol, where each of the four chains is approximately 2,500 mol. wt., and then derivatized to introduce the functional groups onto each of the four arms. Also preferred are analogous poly(ethylene glycol)-like compounds polymerized from di-glycerol instead of pentaerythritol.

Figure 9A:
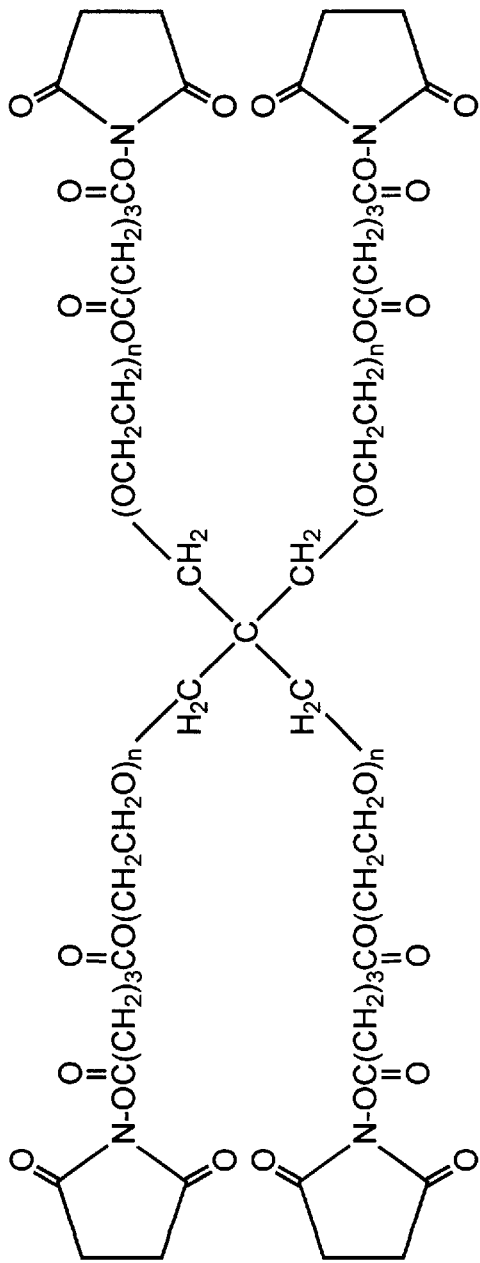
FIG. 9 depicts the structure of COH102 (9a) and COH206 9 b).

When only one of the multifunctionally activated compounds comprises a polymer core, the other compound is a multifunctionally active small organic molecule. Such compounds include the di-functional di-succinimidyl esters and di-maleimidyl compounds, as well as other well known commercially available compounds (Pierce Chemical Co., Rockford, Ill.). In addition, one of skill in the art could easily synthesize a low molecular weight multi-functional reactive compound using routine organic chemistry techniques. On such compound is shown in FIG. 9a, which is a penta-erythritol coupled to four glutarates, with each arm capped with N-hydroxy-succinimidyl esters (NHS). Analogous compounds can be synthesized from inositol (radiating 6 arm), lactitol (9 arm) or sorbitol (linear 6-arm). The end-capped reactive group can just as easily be sulfhydryl, maleimidyl, vinyl-sulfone, etc., instead of NHS. The polymer or the small molecule can carry either reactive end group as long as there are reactive pairs in the composition such as NHS and SH, maleimidyl and SH, etc.

In addition to polyalkylene oxides, e.g. polymethylene, polyethylene and polypropylene, other polymers are also useful as core materials in the practice of the present invention. For example, polyesters, polymethacrylates, polycaprolactones, polyalkenes (such as polybutadiene) are also considered useful. Many of these materials have wide usage in the medical industry. For example, polycaprolactans are elements of Nylon-6; polypropylene is a constituent of medical implants; polymethacrylate is found in polymethyl-methacrylates and poly-hydroxy-methyl-methacrylates, which are constituents of medical implants; and polybutadiene is present in commercial rubber.

An exemplary non-polyalkylene oxide based composition is comprised of two different components, each comprising a different penta-erythritol based compound, such that the two compounds react with one another when mixed together to form a strong matrix. The first compound is penta-erythritol tetrakis (3-mercapto-proprionate) ("PESH-P"), and the second compound is penta-erythritol tetra-acrylate ("PETA"). A large variety of similar molecular structures (4-armed and radially symmetrical) can be synthesized based on penta-erythritol. The length of the molecular chains can be extended, preferably using non-alkyoxyl segments, such as polyester, polymethylene, polyamides, or other materials that are constituents of known biocompatible polymers.

Other radially branching molecules, such as glycerol or lactitol, can be utilized to construct gel-forming materials. The desired structures may be water-immiscible and low molecular weight (350 to about 12,000 mol. wt.) so as to remain liquid. Higher molecular weight gel-forming structures are also contemplated. It is preferred that such compositions are water miscible or water dispersible to be compatible with the use of water as the liquid medium for delivery.

In addition to the branched molecules described above, the compositions of the present invention can be formed from linear molecules as depicted in FIG. 4. Such linear molecules can have molecular weights as high as 100,000 mol. wt., so long as they have biodegradable elements ("O") and sufficient functional groups ("R") as depicted in FIG. 1.

Tensile Strength Enhancer

In order to enhance matrix strength, it is generally desirable to add a "tensile strength enhancer" to the composition. Such tensile strength enhancers preferably comprise micron-size, preferably 5 to 40 microns in diameter and 20 to 5000 microns in length, high tensile strength fibers, usually with glass transition temperatures well above 37° C.

Suitable tensile strength enhancers for use in the present invention include, inter alia, collagen fibers, polyglycolide and polylactide fibers, as well as other organic tensile strength enhancers and inorganic tensile strength enhancers. A particularly useful tensile strength enhancer is Vicryl (polyglycolide:polylactide, 90:10) The use of tensile strength enhancers, which are part of the broader category of "fillers", are well known. For example, "silicone gums", when cross-linked with peroxides, are weak and cheesy, with tensile strengths on the order of only 34 N/cm$^2$. When suitably compounded with reinforcing fillers, the tensile strength of these gums may increase as much as fifty-fold. Lichtenwalner, H.K. and Sprung, M. N., in Mark, H. F., Gaylord, N. G., and Bikales, N. M., Eds., Encyclopedia of Polymer Science and Technology, Vol. 12, p. 535, John Wiley, New York, 1970.

Suitable tensile strength enhancers are those that have inherent high tensile strength and also can interact by covalent or non-covalent bonds with the polymerized gel network. The tensile strength enhancer should bond to the gel, either mechanically or covalently, in order to provide tensile support. Tensile strengths of polyglycolide resorbable sutures are approximately 89,000 N/cm$^2$; that of collagen fibers is 5000–10,000 N/cm$^2$ (Hayashi, T., in Biomedical Applic. of Polym. Mater., Tsuruta, T. et al., Eds., CRC Press, Boca Raton, Fla., 1993).

Reactive Groups and Matrix Linkage

In the present invention, the linkage, Z, comprises a covalent bond that is formed when the functional groups, X and Y, are reacted together. The functional groups can be sulfhydryl, succinimidyl, acrylate, amino, etc. Accordingly, the linkage may be an ester, an ether, a disulfide, or the like. Other functional groups, their reactivity and the bonds formed therefrom are well known in the scientific literature. For example, see Bodanszky, M., Principles of Peptide Synthesis, 2nd ed., pages 21 to 37, Springer-Verlog, Berlin (1993); and Lundbland, R. L., Chemical Reagents for Protein Modification, 2nd ed., Chapter 6, CRC Press, Boca Raton, Fla. (1991). Further examples of pairs of functional groups include, inter alia, sulfhydryl/acrylate, sulfhydryl/succinimidyl, amino/succinimidyl and amino/acrylate.

In addition to the sulfhydryl reactive compounds that form thioester linkages, various other compounds can be utilized that form other types of linkages. For example, compounds that contain methyl imidate derivatives form imido-thioester linkages with sulfhydryl groups. Alternatively, sulfhydryl reactive groups can be employed that form disulfide bonds with sulfhydryl groups, such as ortho pyridyl disulfide, 3-nitro-2-pyridenesulfenyl, 2-nitro-5-thiocyanobenzoic acid, 5,5'-dithio-bis(2-nitrobenzoic acid), derivatives of methane-thiosulfate, and 2,4-dinitrophenyl cysteinyl disulfides. In such instances, auxiliary reagents, such as the hydrogen peroxide or di-tert-butyl ester of azodicarboxylic acid, can be used to facilitate disulfide bond formation.

Yet another class of sulfhydryl reactive groups form thioether bonds with sulfhydryl groups. Such groups include, inter alia, iodoacetamide, N-ethylmaleimide and other maleimides, including dextran maleimides, monobromobimane and related compounds, vinylsulfones, epoxides, derivatives of O-methylisourea, ethyleneimines, aziridines, and 4-(aminosulfonyl-)7-fluoro-2,1,3-benzoxadiazole.

Chain Extenders

Functional groups may be directly attached to the compound core, or they may be indirectly attached through a chain extender. Such chain extenders are well known in the art. See, for example, PCT WO 97/22371, which describes "linking groups" that would be suitable for use as chain extenders in the compositions of the present invention. Chain extenders are useful to avoid stearic hindrance problems that are sometimes associated with the formation of direct linkages between molecules. Alternatively, chain extenders may be used to link several multifunctionally activated compounds together to make larger molecules. In a particularly preferred embodiment, the chain extender can also be used to alter the degradative properties of the compositions after administration and resultant gel formation. For example, chain extenders can be incorporated into one or both of the multifunctionally activated polymers to promote hydrolysis, to discourage hydrolysis, or to provide a site for enzymatic degradation. Chain extenders can also activate or suppress activity of sulfhydryl and sulfhydryl-reactive groups. For example, electron-withdrawing groups within one or two carbons of the sulfhydryl group would be expected to diminish its effectiveness in coupling, due to a lowering of nucleophilicity. Double-bond carbon and carbonyl carbon would be anticipated to have this effect. Bulky nearby groups for either partner are anticipated to diminish coupling rates, due to steric hindrance. Electron-withdrawing groups adjacent to the reactive carbonyl of glutaryl-N-hydroxysuccinimidyl would be anticipated to make this carbonyl carbon even more reactive with the sulfhydryl partner.

Chain extenders may provide sites for degradation, i.e., hydrolysable sites. Examples of hydrolysable chain extenders include, inter alia, alpha-hydroxy acids such as lactic acid and glycolic acid; poly(lactones) such as caprolactone, valerolactone, gamma butyl lactone and p-dioxanone; poly (amino acids); poly(anhydrides) such as glutarate and succinate; poly(orthoesters); poly(orthocarbonates) such as trimethylene carbonate; and poly(phosphoesters). Examples of non-degradable chain extenders include, inter alia, succinimide, propionic acid and carboxymethylate. See, for example, PCT WO 99/07417. Examples of enzymatically degradable chain extenders include Leu-Gly-Pro-Ala, which is degraded by collagenase; and Gly-Pro-Lys, which is degraded by plasmin.

Other general principles that should be considered when designing the compositions of the present invention are as follows: If higher molecular weight structures are to be used, they preferably have biodegradable linkages as described above, so that fragments larger than 20,000 mol. wt. are not generated during resorption in the body. In addition, to promote water miscibility and/or solubility, it may be desired to add sufficient electric charge or hydrophilicity. Such hydrophilic groups can be easily introduced using known chemical synthesis, so long as they do not give rise to gels that swell more than 3–5 fold or that have low tensile strength. In particular, polyalkoxy segments may weaken gel strength.

Optional Composition Constituents

In addition to the functionally activated polymer compound(s) and the tensile strength enhancer, the compositions of the present invention may also contain other compounds, which may be included in one or both of the components of the two-component compositions, or may be separately administered. In one embodiment, these compounds may become covalently incorporated into the IPN itself by becoming crosslinked to one or both of the functionally activated compounds after they are mixed together. In another embodiment, such as would be the case if the compound was unreactive with either of the functionally activated compounds, the compound may be administered in such a way that it becomes physically or ionically associated with the matrix-forming compounds after mixing, and thus become part of the matrix itself.

Additional compounds that may be added are glycosaminoglycans and proteins. Suitable glycosaminoglycans include, inter alia, hyaluronic acid, chitin, chondroitin sulfate A, B, or C, keratin sulfate, keratosulfate and heparin, and derivatives thereof. In another embodiment, proteins can be added for a variety of purposes. For example, collagen may improve biocompatibility of the matrix, including the potential colonization by cells, promotion of would healing, etc. Collagen and any amino group-containing proteins would also contribute to the structural integrity of the matrix by becoming crosslinked thereto along with the other matrix components. In particular, if PEG-succinimidyl esters are used, the amide bonds formed with collagen will be more stable to hydrolytic degradation than the bonds formed by the reaction of succinimidyl esters and sulfhydryls.

Suitable proteins include, inter alia, collagen, fibronectin, gelatin and albumin, as well as peptide fragments thereof. Particularly preferred is collagen, which may be in the form of afibrillar, microfibrillar or fibrillar collagen. Types I and III collagen isolated from bovine corium or human placenta, or prepared by recombinant DNA methods, are suitable. See PCT WO 90/05755 for a description of suitable collagens and collagen derivatives. It should be understood that when adding collagen to the composition, it is important to adjust the concentration of the other composition components to avoid precipitation.

Additional constituents which may be added to the composition include antibiotics, growth factors, hemostatic proteins (such as thrombin, fibrin, fibrinogen, the blood factors, etc.), cells, genes, DNA, etc.

Optional Rigid Nanofibers

The aforementioned optional composition components can be added to the IPNs of the present invention in a variety of forms which are well know to those of the skill of the art. For example, DNA can be added in the form of genomic DNA, oligonucleotides, polynucleotides, dinucleotides and so on. Likewise, the proteinaceous constituents can be added as polypeptides, native proteins, synthetic proteins, protein fragments, etc.

A particularly preferred structure for addition to the IPNs of the present invention is a nanofiber. Many of the aforementioned optional components, and especially methylated collagen, can be easily formed into such a structure. The term "nanofiber" intends a fiber that is usually less than a micron in length. In some instances, these fibers are so small that collagen in this form is considered to be essentially "non-fibrillar". In any event, when incorporated into an IPN consisting of a flexible polymer with a relatively low (less than zero) glass transition temperature such as PEG, a rigid nanofiber with a relatively high (above 25° C.) glass transition temperature imparts additional strength.

Although collagen is a good example of a rigid nanofiber, because it is formed from three polypeptide chains in a triple helix held together by hydrogen bonds, other polymers may be suitable as well. For example, derivatives of other biopolymers which are rod-like, such as tubulin and keratin may be manufactured in rigid nanofiber forms. So long as the structure is a nanometer scale rod-like polymer which is water compatible and preferably has polar and more preferably amino groups on its surface, the rigid nanofiber can be made of a variety of different materials. See, for example, Liu, G., et al., "Diblock Copolymer Nanofibers", Macromolecules 29: 5508–5510 (1996).

Composition Formulation

The compositions of the present invention comprise two separate parts, or "components", which may be in liquid or solid form. In a preferred embodiment, both components are liquids, such that each can be easily applied separately to the site of administration. Accordingly, one of the components may be in the form of a dry powder that becomes mixed with the second component, which is in liquid form, when each are sprayed separately onto the tissue, or by mixing at the tissue site. It is also possible to have both components delivered to the site as powders, to be mixed with buffer at the site of administration.

In an alternative embodiment, both components can be mixed together in a single aqueous medium in which they are both unreactive, i.e. such as in a low pH buffer. Thereafter, they can be sprayed onto the tissue site along with a high pH buffer, after which they will rapidly react and form a gel.

The concentration of the reactive compounds in each of the composition components necessarily depends on a number of factors. For example, if the composition components are each 4-arm PEGs (i.e. PEG-PEG compositions), a concentration of 20–25% by weight in each of the two components before mixing results in a gel after mixing with an elastic modulus, G', of approximately $10^5$–$10^6$ dynes/cm$^2$, which is adequate for use as a surgical sealant. Using methylated collagen and 4-arm succinimidyl PEG, concentrations of 2–4% and 0.2–0.4%, respectively, result in gels with cohesive strengths that are comparable to PEG-PEG gels at 10–15%. Using albumin as one of the components, concentrations of 30% or more achieve a similar cohesive strength. The appropriate concentration of the compound, and other optional ingredients, in each component, and thus the relative concentration of the matrix components in the final gel matrix, can easily be optimized to achieve the desired gelation time and gel strength using routine experimentation. Using the preferred four-arm PEGs described above, the synthetic polymer is generally present at a concentration of 2 to 50% (w/v), and more preferably 10–25%. However, for some applications requiring high strength matrices where flowability of the compositions is not crucial, it is desirable to use PEG at higher concentrations, such as 50% to 70%, more preferably 60%.

The liquid components of the compositions of the present invention are each separately prepared by adding the activated synthetic polymer (in dry form or as a concentrated solution) to a liquid medium. Suitable liquid media include aqueous buffer solutions, such as monobasic sodium phosphate/dibasic sodium phosphate, sodium carbonate/sodium bicarbonate, glutamate or acetate, at a concentration of 0.5 to 300 mM. In general, the sulfhydryl-reactive PEG is prepared in water or a dilute buffer, with a pH of between around 5 to 6. Buffers with pKs between about 8 to 10.5 for preparing the sulfhydryl-PEG component are useful to achieve fast gelation time of compositions containing mixtures of sulfhydryl-PEG/SG-PEG. These include carbonate, borate and AMPSO (3-[(1,1-dimethyl-2-hydroxyethyl) amino]2-hydroxy-propane-sulfonic acid). In contrast, using a combination of maleimidyl PEG and sulfhydryl-PEG, a pH of around 5 to 9 is preferred for the liquid medium used to prepare the sulfhydryl PEG. A particularly preferred composition for hemostatic applications to actively bleeding tissue sites comprises a mixture of maleimidyl and succinimidyl PEG as the first component, and sulfhydryl PEG as the second component. Such compositions produce gels with enhanced biodegradability and superior gel times when compared to compositions having only maleimidyl PEG or succinimicyl PEG alone.

The pH of the aqueous buffer solution that is used for each of the two (or more) composition components should be adjusted using routine optimization to achieve a final pH that is conducive to rapid gelation, without causing instantaneous gelation which interferes with the delivery process. For example, both amino PEG and sulffiydryl PEG need a basic pH to enhance nucleophilicity. The effects of pH on gel time are discussed below in the Examples.

Gel Strength

The compositions of the present invention are formulated to exhibit superior cohesive strength. This generally means that they exhibit at least 10% and preferably 20% of the burst strength of Cyanoacrylate, "Superglue".

Exemplary Formulation made from COH102/206/ Methylated Collagen Plus Glass Wool or Vicryl.

The addition of methylated collagen to PEG formulations, such as COH102/COH206 described below in Example 2, greatly toughens the gel and allows it to resist swelling in saline buffer or water. Because the gel does not swell, it continues to have sufficient inherent tensile strength to remain bonded to fibrous fillers, such as glass wool, Vicryl threads, or silk suture threads.

The combination of COH102/COH206 and methylated collagen can be thought of as "an interpenetrating polymer network". This is because the methylated collagen and the PEG reagents exist as a homogeneous, transparent solution prior to gelation at pH 4–5. The ability of PEG and derivatized collagen to coexist in solution together was a very unexpected discovery. At the point of gelation (triggered by raising the pH), COH102 and COH206 react through their respective reactive groups to form thio-ether linkages. This linkage gives rise to a network of infinite molecular weight, which is a characteristic of polymer gels. COH102 and COH206 alone form gels, but such gels are comparatively weak. When methylated collagen is present, amino groups on the collagen can also react with COH102, forming amide linkages and resulting in a three-way gel of PEG and collagen, which is covalently linked into a network.

The addition of the methylated collagen creates a gel which is robust enough to support the fibrous fillers. If the gel is not strong enough to hold the fibrous filler, it pulls out under tensile loads, and high tensile strength is not achieved. Table 12 below shows that when other polymeric or particulate molecules are substituted for methylated collagen, the bond performance declines. Hence, the methylated collagen, being a relatively rigid molecule, can impart enhanced strength to the relatively dilute PEG hydrogel. Flexible polymers, such as hyaluronic acid, polylysine, and chitosan, although they are relatively high in molecular weight and create relatively viscous solutions, apparently do not have the same rigidity and are therefore less able to absorb tensile stresses and pass these stresses off to the fibrous filler.

In polymer terms, the PEG is a flexible polymer chain which has a low glass transition temperature (temperature at which the polymer is flexible, instead of rubbery and hard); methylated collagen has a higher glass transition temperature (i.e., methylated collagen loses its rigidity, becomes flexible, at about 33–35 deg. C, at which temperature it "melts" to form gelatin, a flexible chain molecule). Because one forms an interpenetrating polymer network (IPN) between a low glass transition temperature polymer (PEG) and a high glass transition polymer (methylated collagen), the result is reinforcement of the former by the latter. If one tries to reinforce PEG with another flexible polymer (such as hyaluronic acid) which ALSO has a low glass transition temperature (i.e., it is flexible at temperatures of interest), one does not achieve reinforcement. (See, for example, Sperling, L. H., Huelck, V., and Thomas, D. A., "Morphology and mechanical behavior of interpenetrating polymer networks", in Polymer Networks, Structural and Mechanical Properties, eds. A. J. Chompff, S. Newman, Plenum Press, NY, 1971, p. 435) The enhanced bonding strength of the final formulation is apparently dependent on several factors: 1) the PEG reagents COH102 and COH206 covalently bond to form a hydrogel; that gel also exhibits excellent bonding to tissue, apparently because of the succinimidyl ester of COH 102, which can bond to amino groups on the tissue (See Table 14); 2) the methylated collagen forms an interpenetrating polymer network with the PEG gel network, reinforcing it; and 3) passes off tensile loads to fibrous fillers such as polylactide/glycolide fibers or glass fibers. Thus, addition of the fibrous fillers is critical to achieving the final desired level of gel tensile strength.

It is contemplated that other derivatives of collagen which remain soluble (molecular, not fibrillar) at pH 4–7, can also impart the same desired properties. For example, other esters of collagen carboxyl groups, such as ethylated, propylated, or benzylated collagen may also function like methylated collagen. Fibrous collagen is less desired; because it forms beady, clumpy domains in the gel and does not impart enhanced tensile strength. Derivatives of collagen which are not soluble at pH 4 or which may not contain free, reactive amino groups, such as succinylated collagen, are also not preferred, because they do not provide the desired properties. Synthetic polymers which exhibit rigidity are almost exclusively water-insoluble, crystalline structures which would exist as micron-scale lumps and not form the intimate, interpenetrating network with the PEG hydrogel that is needed.

Use and Administration

The compositions of the present invention are generally delivered to the site of administration in such a way that the two (or more) individual components of the composition come into contact with one another for the first time at the site of administration, or immediately preceding administration. Thus, the compositions of the present invention are preferably delivered to the site of administration using an apparatus that allows the two components to be delivered separately. Such delivery systems usually involve two-compartment single exit or dual exit spray devices. Alternatively, the two components can be delivered separately using any type of controllable extrusion system, or they can be delivered manually in the form of separate pastes, liquids or dry powders, and mixed together manually at the site of administration. Many devices that are adapted for delivery of two-component tissue sealants/hemostatic agents are well known in the art and can also be used in the practice of the present invention.

Yet another way of delivering the compositions of the present invention is to prepare the two reactive components (or the single reactive component in the case of sulfhydryl-containing components that are designed to form disulfide bonds) in inactive form as either a liquid or powder. Such compositions can then be activated after application to the tissue site, or immediately beforehand, by applying an activator. In one embodiment, the activator is a buffer solution having a pH that will activate the composition once mixed therewith. See Example 7 for a description of a sulfhydryl-containing PEG composition that is maintained at a low pH until administration, then mixed with a high pH buffer at the application site to initiate gelation.

Still another way of delivering the compositions is to prepare preformed sheets, and apply the sheets as such to the site of administration (see Examples).

The compositions of the present invention can be used in a variety of different pharmaceutical applications. In general, the compositions described herein can be adapted for use in any tissue engineering application where synthetic gel matrices are currently being utilized. For example, the compositions of the present invention are useful as tissue sealants, in tissue augmentation, in tissue repair, as hemostatic agents, in preventing tissue adhesions, in providing surface modifications, and in drug/cell/gene delivery applications. One of skill in the art could easily determine the appropriate administration protocol to use with any composition having a known gel strength and gelation time based on the principles described herein and well known scientific principles. A more detailed description of several specific applications is given below:

Tissue Sealants & Adhesives

In a preferred application, the compositions described herein can be used for medical conditions that require a coating or sealing layer to prevent the leakage of gases, liquid or solids. The method entails applying both components to the damaged tissue or organ to seal 1) vascular and or other tissues or organs to stop or minimize the flow of blood; 2) thoracic tissue to stop or minimize the leakage of air; 3) gastrointestinal tract or pancreatic tissue to stop or minimize the leakage of fecal or tissue contents; 4) bladder or ureters to stop or minimize the leakage of urine; 5) dura to stop or minimize the leakage of CSF; and 6) skin or serosal tissue to stop the leakage of serosal fluid.

These compositions may also be used to adhere tissues together such as small vessels, nerves or dermal tissue. The material can be used 1) by applying it to the surface of one tissue and then a second tissue may be rapidly pressed against the first tissue or 2) by bringing the tissues in close juxtaposition and then applying the material. In addition, the compositions can be used to fill spaces in soft and hard tissues that are created by disease or surgery.

Surgical Adhesions

A preferred application is a method of reducing the formation of adhesions after a surgical procedure in a patient. The method entails applying the material onto the damaged tissue or organ either by spraying both components together or by applying previously admixed components or a preformed solid implant The components will react together to form a strong matrix on the tissue surface. The medical procedures include gynecological, abdominal, neurosurgical, cardiac, and orthopedic indications.

Drug Delivery

A preferred application is a method of locally applying a biologically active substance to patients. The active substance can be delivered in conjunction with the two components such that the material can form in situ, or it can be part of a preformed implant. The active substance can be either released through diffusion controlled processes or may be covalently bound to the components such that it will be released as the resulting hydrogel degrades.

The biologically active substances can be any of a variety of organic and inorganic materials, including proteins, carbohydrates, and nucleic acids. Specific examples include enzymes, antibiotics, antineoplastic agents, cytokines, local anesthetics, hormones, antiangiogenic agents, antibodies, neurotransmitters, psychoactive drugs, drugs affecting reproductive organs, and therapeutic oligonucleotides.

Modification of Implants

A preferred application is a method of applying coatings to implants to affect the surface properties of implants or to help adhere implants to tissue surfaces. A coat of components may be applied to 1) vascular grafts, stents to minimize or stop the leakage of blood or serosal fluid from these devices; 2) catheters or breast implants to reduce or stop excessive fibrosis; 3) artificial patches or meshes to minimize excessive fibrosis and to help adhere the implants to tissue surfaces.

Delivery of Cells or Genes

A preferred application of the compositions is to encapsulate and thereby deliver cells or genes, which includes material from natural sources or synthetic DNA, RNA and their respective antisense forms, to a desired site. The cells can include mesenchymal stem cells, epithelial cells and neuroectodermal cells. The cells may either be allogeneic or xenogenic in origin.

EXAMPLES

Example 1

Figure 2A:
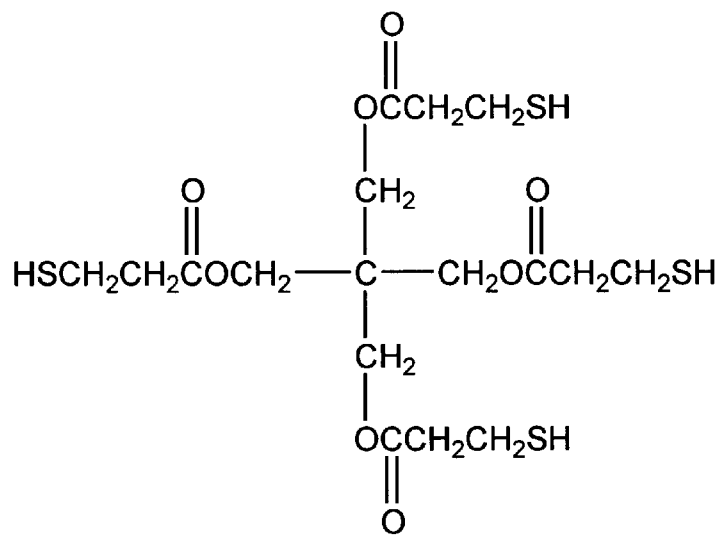
FIG. 2a depicts the structure of penta-erythritol tetrakis (tri mercapto propionate, "PESH-P").
Figure 2B:
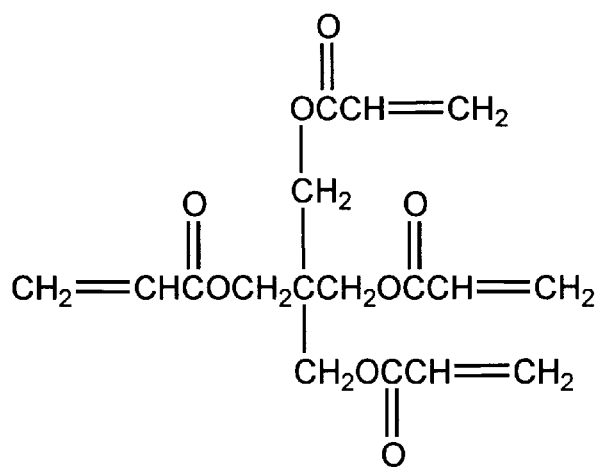
FIG. 2b depicts the structure of penta-erytlritol tetra acrylate ("PETA").
Figure 2C:
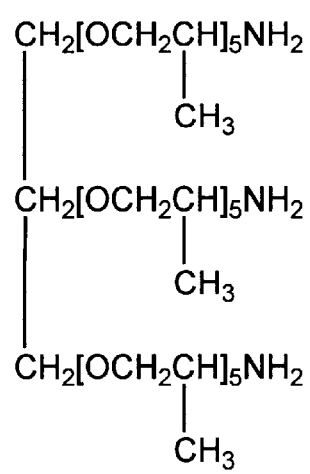
FIG. 2c depicts the structure of T403, which couples to COH102 or acrylates.

Preparation of a Two-Component Penta-Erythritol Based Tissue Sealant Composition Penta-erythritol tetrakis (3-mercapto-proprionate), mol. wt. 489 ("PESH-P", FIG. 2a), 1.08 g, and penta-erythritol tetra-acrylate, mol. wt. 352 ("PETA", FIG. 2b), 1.0 g, are mixed together in the presence of 5 to 10 µg of a poly-oxypropylene tri-amine ("T403", FIG. 2c, Jeffamine, Texaco Chemical Co., Houston, Tex.), which serves as a base.

Figure 3:
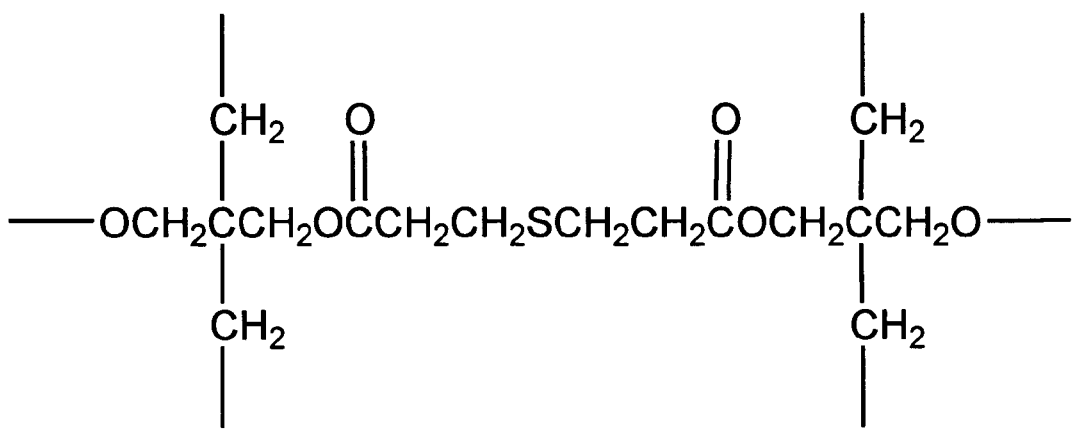
FIG. 3 depicts the bond formation between PESH-P and PETA.

All reactive species are liquids. The PESH-P and PETA are not miscible in water. Accordingly, PETA is warmed to about 40° C. to form a liquid prior to mixing with PESH-P and T403. Within 1 to 5 minutes after mixing, depending on the level of T403, gelation begins. The bond formed between PESH-P and PETA is shown in FIG. 3. The gel is allowed to cure for several hours, followed by one hour of hydration at 37° C. Thereafter, the tensile strength of the gel is 0.88+/−0.3 MPa. When such gels are left in physiological saline, pH 6.7, they are stable for more than 40 days, and only swell about 20%. Burst strength data shows only moderate adhesion to hide grindate. This would be expected, since there is no chemical bonding of sulfhydryl or acrylate to protein using PETA-P/PESH mixtures. In three tests of burst strength, burst pressures of 20–40 mm Hg were observed.

Example 2

Tensile Strength of Various Compositions

Figure 4A:
FIG. 4a depicts the structure of poly tetramethylene oxide di-amine, which couples to COH102 or acrylates.
Figure 4B:
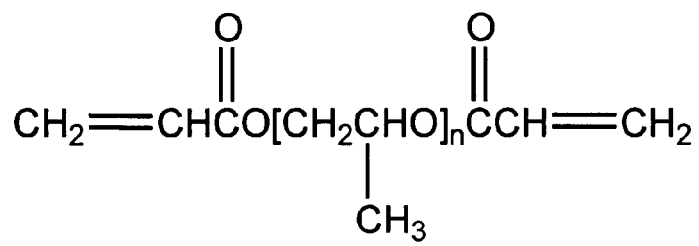
FIG. 4b depicts the structure of polypropylene oxide di-acrylate, which couples to thiols or amino groups.
Figure 4C:
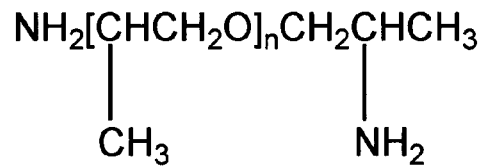
FIG. 4c depicts the structure of polypropylene oxide di-amino, which couples to COH102 or acrylates.

Materials and Methods:

Penta-erythritol polyethylene glycol ether tetra-thiol, 10,000 mol. wt. ("COH206"), penta-erythritol polyethylene glycol ether tetra succinimidyl-glutarate, 10,000 mol. wt. ("COH102"), and penta-erythritol polyethylene glycol ether tetra amino, 10,000 mol. wt. ("COH204"), were purchased from Shearwater Polymers, Inc. (Huntsville, Ala.) Cyanoacrylate, "Superglue", was purchased over the counter. Gelatin, 70–100 Bloom, was purchased from Sigma (Saint Louis, Mo.) Sulfo-ethylene glycol bis succinimidyl succinate ("S-EGS"), dimethyl suberimidate ("DMS"), and dissuccinimidyl glutarate ("DSG") were purchased from Pierce Chemical Company, Rockford, Ill. Polyethylene glycol ("PEG") 200 mol. wt. di-acrylate ("PEG-di-acrylate"); PEG, 1,000 mol. wt. di-methacrylate ("PEG-di-methacrylate"); and 2-hydroxy-ethyl methacrylate ("HEMA") were purchased from Polysciences, Inc., Warrington, Pa. Polypropylene ("PPO"), 540 mol. wt. di-acrylate ("PPO-di-acrylate"); PPO, 230 mol. wt. bis-2-aminopropyl ether ("PPO-di-amino 230"); PPO, 2,000 mol. wt. bis-2-aminopropyl ether ("PPO-di-amino 2,000"); poly-tetrahydrofuran bis (3-aminopropyl) ("PTMO"), 350 mol. wt. ("PTMO 350"); PTMO, 1,100 mol. wt. ("PTMO 1,100"); PESH-P, 489 mol. wt.; PETA, 352 mol. wt.; and potassium meta-bisulfite were purchased from Aldrich Chemical Company, Milwaukee, Wis. Ammonium persulfate was purchased from Biorad, Inc., Richmond Calif. Methylated collagen was prepared from purified bovine corium collagen, following a method modified from U.S. Pat. No. 4,164,559 (see Example 7.) The structures of PTMO (also called polytetramethylene oxide di-amine) PPO di-acrylate and PPO di-amine are shown in FIGS. 4a, 4b and 4c, respectively.

Gels Were Prepared as Follows:

a. COH102/COH206: 100 mg COH102 were dissolved in 400 µl 0.5 mM sodium phosphate, pH 6.0. 100 mg COH206 were dissolved in 400 µl 300 mM sodium phosphate, pH 7.5. The two solutions were mixed in a beaker and poured into a mold of approximately 8×0.5×0.5 cm. Gelation occurred in 2–3 minutes. The sample was left at room temperature until dry. The dried matrix was removed from the mold, and hydrated at 37° C. for one hour prior to the tensile strength test.

b. COH102/COH204: The sample was prepared as described in a., except that the COH204 was substituted for COH206.

c. PETA/PESH-P: The sample was prepared as described in Example 1.

d. Gelatin gels: 20% gelatin in sodium phosphate/sodium carbonate buffer, pH 9.6, was mixed with different compounds as indicated below and described in a., assuming 10–20 moles of active amino per mole of gelatin, and using stoichiometric levels of the other compound.

e. COH102/PPO-di-amino 2,000/PEG-di-acrylate: 615 mg COH102 was dissolved in 923 μl ethanol, and mixed with 246 μl PPO-di-amino 2,000 and 246 μl PEG-di-acrylate as described in a.

f. PETA/PPO-di-amino 230/PPO-di-amino 2,000: 500 μl PETA, 630 μl PPO-di-amino 230 and 150 μl PPO-di-amino 2,000 are mixed together as described in a.

g. COH102/PTMO: The gel was prepared as described in e, with PTMO 1,100 substituted for the PPO-di-amino 2,000.

h. Cyanoacrylate: The glue was extruded onto water and immediately hardened.

i. HEMA: 1.3 ml HEMA and 64 μl PEG-di-acrylate were dissolved in 600 μl of 150 mM sodium phosphate buffer, pH 7.4, and mixed with 40 mg ammonium persulfate in 100 μl water. The mixture was heated to 60–80° C. for 4 hours.

j. COH102/COH206/methylated collagen: 25 mg methylated collagen, 100 mg COH102, and 100 mg COH206 were dissolved in 1 ml of 0.5 mM sodium phosphate, pH 6.0.

Tensile Strength Measurements

The ends of the dried gels were secured, and then the central regions of all samples were rehydrated for approximately 1 hour in physiological saline buffer, pH 6.7 at 37° C. prior to the test. Then, the matrices were extended to the point of breakage in an Instron Model 4202 test apparatus (Instron, Inc., Canton, Massachusetts) that was fitted with a 100 N load cell. The peak load was recorded and converted into ultimate stress using the measured cross-section of the sample at the break point. Data were also plotted as stress v. strain, using strain $=\Delta L/L_0$, where $\Delta L$ is the extension, and $L_0$ is the original sample length.

TABLE 1

Tensile strength measurements

| Material | Tensile Strength (N/cm$^2$) | |
|---|---|---|
| HEMA | >393 | |
| Cyanoacrylate | 385 | |
| PETA/PESH-P | 78 | (n = 10) |
| PETA/PTMO-di-amino 350/1,100 | 26 | (n = 2) |
| PETA/PTMO-di-amino 1,100 | 34 | |
| PETA/PPO-di-amino 230/2,000 | 36 | (n = 2) |
| PESH-P/PPO-di-acrylate | 20 | |
| COH102/COH206/methylated collagen | 37 | (n = 3) |
| COH102/PPO-di-amino 2,000/PEG-di-acrylate 200 | 10 | (n = 2) |
| COH102/PTMO-di-amino | 4 | (n = 2) |
| COH102/T403 | 5 | |
| COH206/PEG-di-acrylate | 8 | |
| COH/206/PEG-di-methacrylate/PEG-diacrylate | 4 | |
| COH206/PEG-di-methacrylate | 26 | |
| Gelatin/DMS | 6 | |
| Gelatin/S-EGS | 6 | (n = 2) |
| Gelatin/PETA | 5 | |
| Gelatin/DSS/T403 | 3 | |
| COH102/COH206 20% | 5 | (n = 4) |
| COH102/COH206 10% | 10 | |

Example 3

High-strength Adhesives Based on COH102 and COH206 and a Comparison with Adhesives Prepared from PETA, PESH-P, and GLYC-20HS Summary:

Several types of gels were investigated as potential suture replacement formulations. Gels based on penta-erythritol derivatives exhibited high cohesive, but poor adhesive strength. Gels based on a 3-armed succinimidyl glycerol-PEG exhibited low cohesive strength, but good adhesive strength. Gels based on 60% aqueous (w/v) COH102/COH206, to which various fibrous materials were added, such as fibrous insoluble collagen, polyglycolide sutures and glass wool, exhibited both good cohesive and adhesive strengths.

High strength medical adhesives are of interest as suture-replacements in closure of surgical incisions. In particular, gels formed from PETA and PESH-P were shown to have tensile strengths about 10X greater than those formed from 20% (w/v) solutions of COH102 and COH206. When PETA-PESH-P gels were supplemented with fibrous or particulate polymers, gels with even higher tensile strengths were observed.

This experiment describes the adhesive properties of PETA/PESH-P and related gels, as well as both adhesive and tensile properties of a formulation of COH102 and COH206 at 60% (w/v), to which collagen and other polymers are added. Also described are properties of gels formed from a 3-arm glycerol succinimide (NOF Corp., Japan) and the above reagents.

Materials and Methods:

PETA, PESH-P, and penta-erythritol tetrakis (3 mercaptoacetate) (PESH-A), polyethylene, surface activated 180 μ particle size, and polybutadiene, epoxy functionalized, epoxy E.W. 260, were purchased from Aldrich Chemical Co., Milwaukee, Wis. GLYC-20HS (poly-oxyethylene glyceryl ether) succinimidyl succinate 2600 mw), DEPA-10H (poly-oxyethylene bis-amine 1040 mw) were obtained from NOF Corporation, Japan. COH102 and COH206 were reagent grade from Shearwater Polymers, Huntsville, Ala. Polyethylene-co-acrylate-succinimidate (PE-AC-S) was synthesized from a polyethylene-co-acrylate (approx. mol. wt. 400K with 5% acrylate) purchased from Aldrich Chemical Company, Milwaukee, Wis. Kensey-Nash insoluble collagen (Semed F) was purchased from Kensey-Nash Corporation, Exton, Pa. Collagen Matrix, Inc, Franklin Lakes, N.J., supplied a second type of insoluble collagen. Prolene 7–0 sutures were manufactured by Ethicon Corporation. Coarse fibered collagen sheets were cut from the same coarse fibered bovine corium collagen as that used for the burst test as described in Prior, J. J., Wallace, D. G., Hamer, A., and Powers, N., "A sprayable hemostat containing fibrillar collagen, bovine thrombin, and autologous plasma", Ann. Thor. Surg. 68, 479–485 (1999). These collagen sheets served as a tissue model for further studies. Smaller fiber collagen was prepared from re-precipitated pepsin-digested bovine corium collagen manufactured by Collagen Aesthetics, Inc., Palo Alto, Calif. Glass wool was purchased from VWR Corporation. Poly-glycolide sutures, non-coated ("Dexon S") were from Davis and Geck.

Gel formation for tensile strength measurements is described above in Example 1. For burst tests, the apparatus used is described in Wallace, et al., supra. Approximately 1 ml of total formula was sprayed or spread by spatula onto the coarse fibered collagen sheet substrate and allowed to set. Water pressure was applied after the formulation had reached the texture of a relatively firm rubbery solid (no longer tacky), and the pressure to rupture the seal was recorded as mm Hg.

60% gels of COH102 and COH206 were prepared as follows: COH102 was dissolved at 60% (w/v) in S-buffer (0.5 mM sodium phosphate, pH 6.0) and COH206 was dissolved also at 60% in 300 mM sodium phosphate at pH 7.5 or 8.9; or in 117 mM sodium phosphate, 183 mM sodium carbonate, pH 9.6 ("PC buffer"). In some cases the above ratio of phosphate and carbonate were altered to give pH 9.44 for a faster set time. The pH used in each case was determined by the rate of gelation desired. Various additives were added to such a base formulation; e.g., Kensey-Nash and smaller fiber size collagen was added at 28 mg/ml of final gel; glass wool was added at 25 mg/ml; and polyglycolide sutures, at 40 mg/ml.

Results and Discussion:

The results are discussed below and shown in Tables 2, 3 and 4 that follow. A tensile strength of >60 N/cm$^2$ is considered to be "strong". A burst strength of >50 mm Hg is considered to be "good adhesion".

Gels of PETA and PESH-P had shown good tensile strengths (Example 1). However, when they were tested for adhesion to a hydrated simulated tissue (coarse fibered collagen sheets) in the burst test, they exhibited poor adhesion (<50 mm Hg burst pressure). As shown below in Table 2, the formulation was then modified to contain water soluble GLYC-20HS and DEPA-10H, or the pair COH102 and COH206 (which alone in aqueous media gave good adhesion to the collagen sheets). These materials had good tensile strength (manual evaluation), but again poor adhesion to the collagen sheets. The gel formed from GLYC-20HS and DEPA-10H also had poor adhesion when no water was present in the formula. A different result may be observed when these reagents are dissolved in aqueous buffers, since they are water soluble.

However, when GLYC-20HS was the major component by mass, the gels were weak but exhibited good adhesion in the burst test. Using these particular combinations of components, it appeared that one could achieve either high tensile strength or high adhesive bonding, but not both.

TABLE 2

Tensile strength and burst strength of gels prepared with NOF 3-arm glycerol succinimide

| Material | Tensile Strength (N/cm$^2$) | Burst Strength (mmHg) |
| --- | --- | --- |
| PETA 500 mg PESH-P 540 µl T403 5 ul | >60 | 23 |
| GLYC-20HS 50 mg PETA 500 mg PESHP 540 µl DEPA-10H 9 mg | >60 | 14.5 |
| PESH-A 216 ul PETA 240 mg GLYC-20HS 40 mg | >60 | 11 |
| PETA 400 mg COH102 100 mg PESH-P 440 µl COH206 100 mg DEPA-10H 8 mg | >60 | 15 |
| GLYC-20HS 640 mg DEPA-10H mg | — | 25 |
| GLYC-20HS 400 mg PESH-A 36 µl T403 10 µl | <30 | >120 |
| GLYC-20HS 400 mg PETA 50 mg PESH-A 72 µl T403 20 µl | <30 | 166, 194 |
| GLYC-20HS 200 mg T403 19 µl PESH-P 18 µl | <30 | 55 |

The ability of a succinimidyl-derivatized polyethylene (PE-AC-S) to act as an effective tensile strength enhancer for PETA-PESH-P gels and for COH102/206 gels was also assessed (Table 3). This material did not increase the tensile strength of these gels, perhaps because it was not an extended filament, i.e. its aspect ratio was not high enough.

TABLE 3

Polyethylene-co-acrylate-succinimide ("PE-AC-S") as a Tensile Strength Enhancer

| Material | Tensile Strength (N/cm$^2$) |
| --- | --- |
| PETA 400 mg PESH-P 432 µl T403 8 µl PE-AC-S 20 mg | 80 (same as control with no PE-AC-S) |
| COH102 COH206 (60%) + KN collagen (28 mg/ml) + PE-AC-S (40 mg/ml) | 38 (weaker than control with no PE-AC-S) |

Table 4 also summarizes results with COH102 and COH206 plus Kensey-Nash fibrillar collagen, which exhibited an enhanced tensile strength over 20% and 60% (w/v) gels of COH102/206 alone. Furthermore, the COH102/COH206/collagen formulation possessed good adhesive bonding to the collagen sheets. Other additives, such as hide grindate and Prolene 7-0 sutures also enhanced the gel strength over controls. Some fillers, such as small fiber collagen, polyethylene, and polybutadiene, did not exhibit tensile strength enhancing properties. Finally, some fillers or combinations thereof, such as glass wool and insoluble collagen plus poly-glycolide sutures, exhibited a significant enhancement of tensile strength, exceeding that seen with cyanoacrylate (385 N/cm$^2$) (Example 1). Limited burst strength data were collected, but they confirm that all these COH102/206 (60%) formulations are highly adhesive to collagen surfaces, and thus would be expected to adhere to tissues as well.

As shown in Table 4, the P-HEMA hydrogel is described in Santin, M., et al., "Synthesis and characterization of a new interpenetrated poly (2-hydroxyethylmethacrylate)-gelatin composite polymer", Biomaterials 17, 1459–1467; and the gelatin-PEG-di-acrylate is described in Nakayama, Y., and Matsuda, T., "Photocurable surgical tissue adhesive glues composed of photoreactive gelatin and poly(ethylene glycol) diacrylate", J. Biomed. Biomat. Res. (Appl. Biomater.) 48, 511–521 (1999).

TABLE 4

Tensile strength and burst strength tests

| Material | Tensile Strength (N/cm$^2$) | Burst Strength (mm Hg) |
| --- | --- | --- |
| COH102/206 20% GEL | 2–12 | 100–200 |
| pHEMA HYDROGEL* | 3 | |
| GELATIN-PEG-DI-ACRYLATE** | 5–16 | 151 ± 34 |
| PETA-PESH-P | 50–170 | 14, 23 |
| PETA-PESH-P + KN collagen | 140–200 | |
| COH102/206 (60%) + KNcollagen | 123 ± 39 (n = 7) | 268, 216 |
| COH102/206 (60%) + KNcollagen + 7-O Prolene sutures | 180 | |

TABLE 4-continued

Tensile strength and burst strength tests

| Material | Tensile Strength (N/cm$^2$) | Burst Strength (mm Hg) |
|---|---|---|
| COH102/206 (60%) + hide grindate | 197, 78 94 | |
| COH102/206 (60%) no filler | 27 | |
| COH102/206 (60%) + Small fiber collagen | 27 | |
| COH102/206 (60%) + 7-O Prolene sutures coated | 58 | |
| COH102/206 (60%) + polyethylene | 14 | |
| COH102/206 (60%) + polyethylene + poly-butadiene | 58, 30 28, 21 | |
| COH102/206 (60%) + glass wool | 745 161 | 156 |
| COH102/206 (60%) + KN collagen + Dexon S sutures | 531 | |
| COH102/206 (60%) + Collagen Matrix collagen + Dexon S sutures | 718 | 376 |

Figure 5:
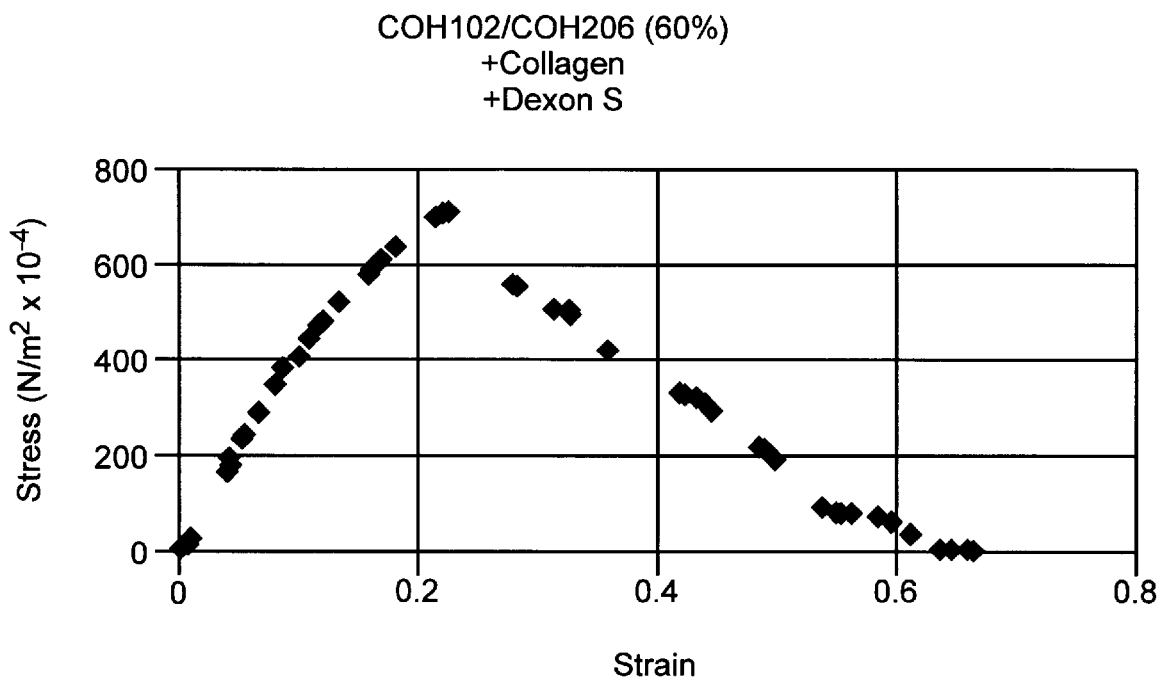
FIG. 5 depicts the results of Example 3.

FIG. 5 depicts the tensile test of COH102/206 (60%) plus 28 mg/ml Collagen Matrix collagen plus 40 mg/ml cut pieces of Dexon S uncoated polyglycolide sutures (4-0). The measured tensile strength was higher than 700 N/cm$^2$, and the measurement was interrupted when the sample began slipping out of the testing device (downward slope.)

Example 4

Collagen Sheet Composites Containing Active PEG
Summary

COH102 and COH206 can be dissolved together in ethanol without reaction. The ethanol solution can be evaporated to dryness, leaving a reactive PEG powder. When placed in PC buffer, pH 9.6, the powder gels instantly. This finding was then used to develop an adhesive sheet. Collagen sponges and coarse fibered collagen sheets coated with sponges were impregnated with ethanol solutions of COH102 and COH206. After drying, such reactive PEG sheets were able to bond to a coarse fibered collagen sheet. Burst strengths of about 300 mm Hg were observed after 10 min at pH 7.

Adhesive sheets were also prepared that consisted of a course fibered collagen backing (prepared as described in Example 3) to which was bonded a collagen sponge. The sponge layer was impregnated with the reactive PEG powder. When such sheets were placed dry onto a second coarse fibered collagen sheet wetted with pH 9.6 buffer, a strong bond was formed in as little as 30 seconds. Bonding of the adhesive sheet to the second collagen sheet was measured by the burst test. Burst strengths up to 500 mm Hg were observed.

Materials and Methods

Coarse fibered collagen sheets were prepared as described elsewhere herein. Collagen sponges were attached to the collagen sheet by extruding a slurry of reconstituted fibrillar collagen on top. The reconstituted collagen slurry was prepared by diluting outdated Zyderm II collagen (65 mg/ml protein, Collagen Aesthetics, Inc., Palo Alto, Calif.) with water to achieve a 20 mg/ml dispersion. Approximately 7 cm$^2$ of sheet were covered per ml of slurry. Once the collagen slurry was extruded onto the coarse fibered collagen sheets, the composite was frozen and then freeze dried. After freeze-drying, a porous collagen sponge remained adherent to the collagen sheet. To the dry sponge was added dropwise an alcohol solution of COH102 and COH206. The latter was prepared by adding 200 mg of COH102 and 200 mg COH206 each to 1.8 ml of absolute ethanol (dried over molecular sieves). Dissolution of both PEG compounds in ethanol was achieved by gentle warming and stirring (up to about 40° C.). The two solutions were then mixed. One ml of ethanol solution was used to cover about 10 cm$^2$ of sheet. The sponge-collagen sheets, wetted with the PEG solution in ethanol were then dried briefly in a vacuum chamber. When bulk solvent was gone, the sheets were transferred to a lyophilizer for several hours to remove solvent residues. The dry sheets were stored at $-20°$ C. under dry argon.

To test bonding to a second coarse fibered collagen sheet, a burst test was performed. The test sheet of collagen was wetted with PC buffer, pH 9.6 and secured into the sample cell. Additional buffer (0.1 to 0.2 ml) was applied to the sheet. Then the active PEG sponge sheet (prepared as above; 1.2 x 1.2 cm) was placed, sponge side down on the test collagen sheet (size of defect: 2 mm). The two sheets were manually held in place for 2–3 seconds to assure good contact and hydration of the active PEG sheet. Then the two sheets were left to incubate at room temperature until water pressure was applied from below. The pressure required to rupture the seal was recorded.

Results

Table 5 shows that very high bonding strengths can be achieved at pH 9.6, compared to control sheets with no active ingredients. High bond strengths are observed even at short times. The long-term stability of the bond was examined qualitatively: a bonded pair of sheets was removed from the burst test apparatus and placed in 100 ml of water at 33° C. The bond was still intact and apparently strong, even 30 hours later.

TABLE 5

Burst strengths of active PEG sheets apposed to coarse fibered collagen sheets

| Material | Incubation Time (min) | Burst Strength (mm Hg) |
|---|---|---|
| Sheet (control) | 0.5 | 5 |
| Sheet + Sponge (control) | 0.5 | 17 |
| Active PEG + Sheet + Sponge | 0.5 | 360, 391 |
| Active PEG + Sheet + Sponge | 1.0 | 477, 531 |
| Active PEG + Sheet + Sponge | 3.0 | 276, 231 |

Table 6 shows the effect of lowering the pH of the hydrating buffer. The strength of the bond was pH dependent, and much weaker bonding was observed at pH 7.5. However, bond strengths at lower pHs were improved by allowing longer (3 to 10 minutes) for bond formation, which may be acceptable for certain applications.

The mode of failure was not always evident. In some cases, the test sheet became dislodged from the test clamp without damaging the bond. These results were not reported. If the test sheet remained securely clamped, it appeared that failure was between active sheet and test sheet. In some cases, the active sheet was lifted and water spurted from the hole. In other cases, water appeared at the margins of the test cell, but its source was not clear.

TABLE 6

Burst strengths of active PEG sheets apposed to coarse fibered collagen sheets

| Material | pH* | Incubation Time (min) | Burst Strength (mm Hg) |
|---|---|---|---|
| Active PEG | 8.9 | 0.5 | 121 |
| + Sheet | 8.9 | 1.0 | 191 |
| + Sponge | 8.9 | 1.0 | 191 |
|  | 8.9 | 3.0 | 298 |
|  | 7.5 | 1.0 | 2 |
|  | 7.5 | 3.0 | 50 |
|  | 7.5 | 10.0 | 279 |

*pH 8.9 buffer was 300 mM sodium phosphate; pH 7.5 buffer was 300 mM sodium phosphate.

Example 5

Additional Studies on Adhesive Sheets Containing Active PEG

Summary

Adhesive sheets were prepared from COH102/COH206, Zyderm collagen, and Kensey-Nash (Semen F) collagen. Such sheets showed good burst strengths when bonded to coarse fibered collagen sheets.

A shear failure bonding test was developed. In this test, the bond strength of active PEG adhesive sheets were comparable to cyanoacrylate (SUPERGLUE). This experiment describes the preparation of adhesive sheets from biocompatible materials, including implantable grade Kensey-Nash collagen. Also reported herein are comparative results of various formulations in a shear failure test.

Materials and Methods:

Active sheets were prepared from coarse fibered collagen sheets, reconstituted collagen, and COH102 and COH206, as described in Example 4.

Active sheets from Kensey Nash collagen were prepared as follows: collagen (4 g) was added to 200 ml of de-ionized water adjusted to pH 2 with HCl. Stirring with an overhead impeller was maintained for 6 days. The fibers became swollen and dispersed, creating an almost coherent mass. The slurry was poured into 9 cm diameter square polystyrene weighing boats (about 15 ml per boat to cover the bottom). The poured slurry was left in an incubator at 33 to 37° C. to dry. Sheets formed on the surface of the weigh boats. In some cases such sheets were coated with Zyderm collagen (slurry in water at 20 mg/ml), frozen, and freeze-dried. Such dried sheets, coated with a thin sponge-like layer of Zyderm collagen were then activated with an ethanol solution of COH102 and COH206 (each component at 10% w/v concentration). These were referred to as "acidic KN sheets". An alternative procedure utilized dried Semed F sheets (dried from acidic slurry), coated once with Zyderm collagen sheets, and incubated for 3 hours in water adjusted to pH 9–10. Additional sodium hydroxide was added as necessary to keep the solution plus sheets at pH 9- 10. The sheets were recovered from the solution and dried overnight at 37° C. The sheets were then re-coated with Zyderm collagen at 12 mg/ml, frozen, freeze-dried, and finally impregnated with active PEG in ethanol to yield the dried, active samples, termed "basic KN sheets".

Figure 6:
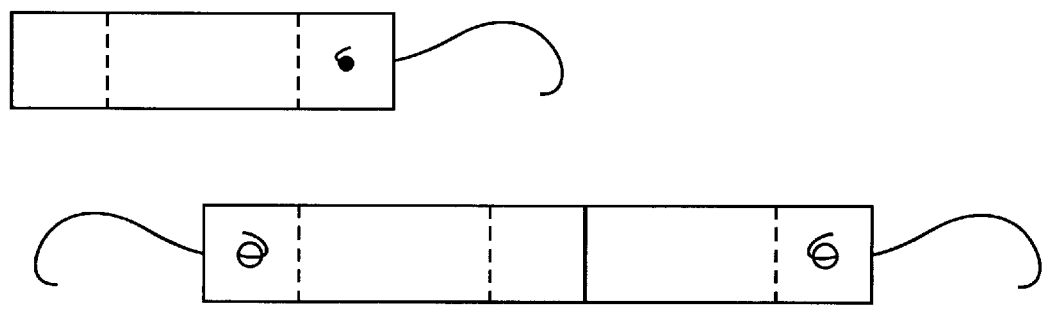
FIG. 6 depicts the apparatus used for shear failure tests of Example 5.

A shear failure test for active sheets was developed using the devices depicted in FIG. 6. Coarse fibered collagen sheets either activated with PEG or as normally prepared for the burst test, were cut to 1×3 cm sizes (termed "strips"). Plastic tabs or adhesive tape was secured over one end, covering a 1 cm square area of the strip. The plastic tabs were secured to the hide grindate strip with cyanoacrylate glue. A hole approximately 2 mm in diameter was pierced in the plastic tab or in the tape. Over a 1 cm square area of a collagen sheet was placed approximately 300 μl of pH 9.6 PC buffer. An active PEG/collagen sheet was then placed on the buffer wetted hide grindate and held with light pressure for 30 sec. In this way the bonded surface was 1 cm square. Hooks were then placed through the holes at the end of each strip, and the bonded strips were suspended to a suitable support. To the lower hook were added metal washers (average weight per washer: 1.63 g) to incrementally increase the shearing force on the bonded surface. The weight required to pull the bonded surface apart was recorded. Variations in the nature of the bonding surfaces and bonding formulations were studied, including using control strips containing collagen sponge on the surface but no active PEG and also bonding of hide grindate strips with cyanoacrylate.

One set of samples involved the bonding of one untreated hide grindate strip to a collagen sponge-coated strip (containing no active PEG). Another set of samples were performed with the same pairs of strips, but this time a COH102/COH206 mixture was added to the apposed strips and allowed to gel. The gelling mixture was as follows:

10 mg COH102 plus 40 μl pH 6.0 0.5 mM phosphate buffer 10 mg COH206 plus 40 μl pH 8.9 300 mM phosphate buffer Such a mixture gels in about 15 seconds, which allows ample time to add the gel mixture to one strip, press the second strip on top, and wait 30 sec for gelation to occur.

For bonding of strips with cyanoacrylate, the test strip was first moistened with PC buffer (200 μl for a 1 cm square area). Then a second strip coated with cyanoacrylate was pressed on top of the first. As with active PEG sheets, only moderate pressure was used to maintain apposition during the 30 sec bonding time.

Results:

Acidic KN sheets and basic KN sheets were subjected to burst testing; 1 cm square pieces were placed over the test hide grindate sheet already wetted with PC buffer. Acidic KN sheets exhibited very low burst strengths (2 and 4 mm Hg). Basic KN sheets gave values similar to previous results with coated collagen sheets (324,286, and 311 mm Hg).

The shear failure method was used to compare bonding of collagen sheets under several conditions (Table 7). For sheets bonded by COH102/COH206, very poor bond strengths were observed. Active PEG sheets exhibited bond strengths similar to that observed with cyanoacrylate.

TABLE 7

Shear Failure of Bonds for Various Sheet Materials

| Material | Bond Rupture Force (g) |
|---|---|
| Sheet + Sponge (control) | 55.4, 53.8 |

TABLE 7-continued

Shear Failure of Bonds for Various Sheet Materials

| Material | Bond Rupture Force (g) |
|---|---|
| Sheet + COH 102/ COH206 | 14.7, 13.0 |
| Sheet + Cyanoacrylate | 272 |
| Sheet + Active PEG | >217, >466* |

*Ultimate bond strengths not determined; in both cases the collagen sheet tore, or the fixation of hooks failed, not the bonded area.

Example 6

Methods for synthesis of high-strength bio-adhesives

Figure 7A:
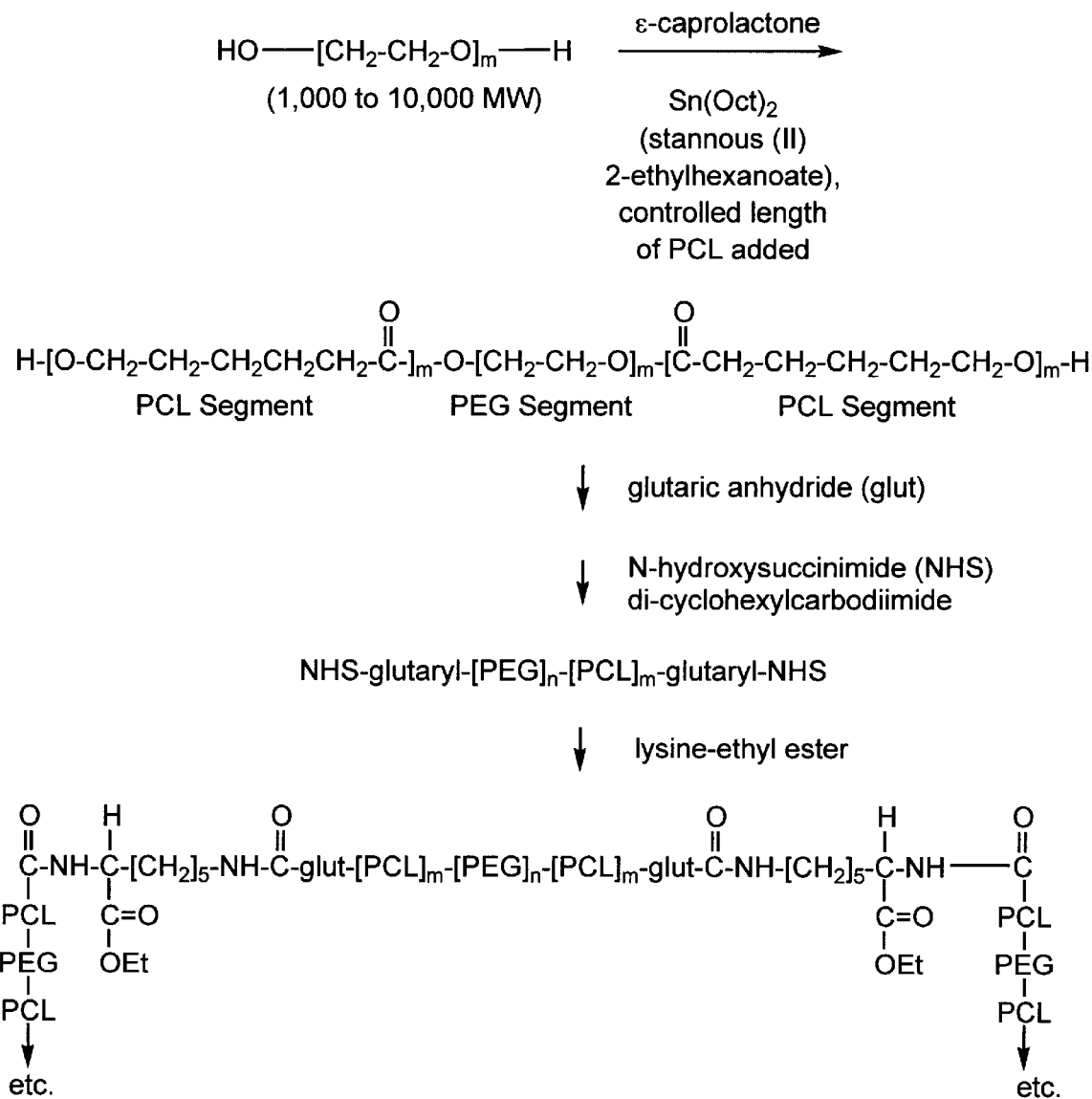
FIGS. 7 and 8 depict that synthetic schemes of Example 6.
Figure 7B:
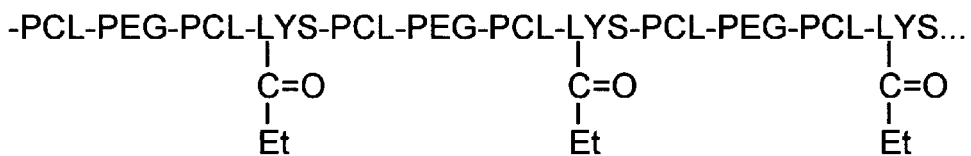
Figure 7B:
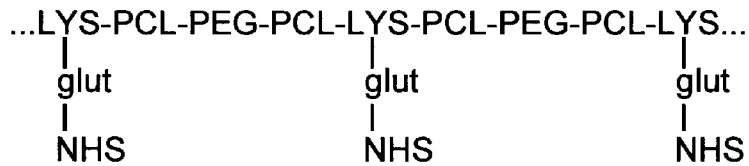

This example describes the synthesis of a copolymer of polyethylene glycol (PEG) and poly-caprolactone (PCL) containing pendant N-hydroxy-succinimidyl groups.
Scheme 1 (FIG. 7):

Di-functional PEG of variable mol. wt. is chosen and coupled to PCL by a controlled ring-opening polymerization to add PCL of fixed and chosen mol wt. (Hedrick et al, Macromolecules 1998, 31, 8691–8705). The terminal —OH groups on the PCL are converted to glutaryl-succinimidyl (Abuchowski et al, Cancer Biochem 1984, 7, 175–180). Lysine ethyl ester is added to give a linear polymer with repeating PEG, PCL, and lysine segments. The lysine segment has a pendant carboxyl ester. The ester is hydrolized to give a free carboxyl group (Nathan et al. Macromolecules 1992, 25, 4476–4484). Then, the carboxyl group is converted to glutaryl-succinimidyl (Abuchowski).

Figure 8A:
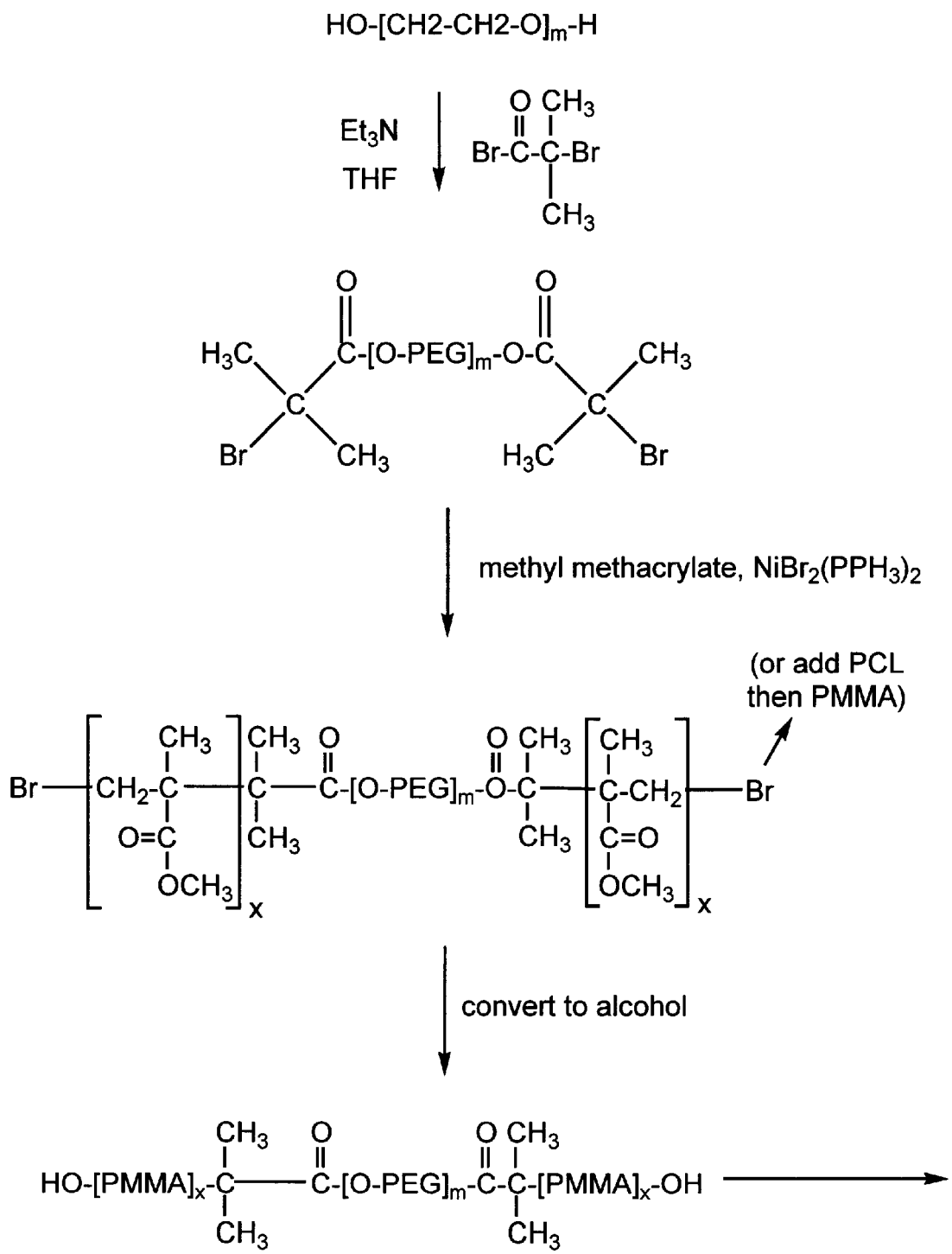

This scheme produced a linear chain with pendant reactive groups (NHS), with degradable links (PCL), with water-soluble groups (PEG). Polymer toughness can be increased by adding long PCL elements versus short PEG elements; however, PEG must be long enough to assure water solubility, which can be determined empirically.
Scheme 2 (FIG. 8):

A similar linear chain with pendant reactive groups, but with PMMA (polymethylmethacrylate) repeating segments. Di-functional PEG of variable but selected mol. wt. is activated with 2-bromo-2-methyl propionyl Br and a controlled segment of PMMA is grown off each end. The terminal contains a Br group which can be converted by standard organic chemical methods to an —OH group and further derivatized to glutaryl-NHS, reacted with lysine ethyl ester as in Scheme 1, and finally, the pendant carboxyl ethyl ester is hydrolyzed to free carboxylate and derivatized to glutaryl NHS, again to give an analogous copolymer with different physical properties (e.g., PMMA is known to have high tensile strength). Sufficient PEG functionality can be provided for water solubility. It may be necessary to build PEG-PCL-PMMA-lys repeating units, so that PCL will provide the necessary bio-degradable linkages. Construction of such segments has been described in Hedrick.

Another approach to reinforced polymers is described by Liu, et al., Macromolecules, 29:5508 (1996). One can synthesize a PMMA block which also contains monomers such as 2-cinnamoylethyl methacrylate (CEM). The following structure is illustrative: A diblock polymethacrylate is synthesized that contains a water-soluble block, such as hydroxyethylmethacrylate (HEMA) plus some amino and carboxyl containing monomers, such as amino-ethyl methacrylate (AEM) and mono-2-(acryloxy)ethylsuccinate (ARS), PLUS a water-insoluble block, such as poly-MMA-co-CEM. When this polymer is in water or a polar medium, the MMA-CEM block will avoid water and associate into separate domains. As outlined by Lie, et al., it is possible to alter the ratio of water-soluble and water-insoluble blocks in the polymer to obtain different domain structures. The associated, water-avoiding domains may take up micellar (sphere-shaped), rod-like, or plate-like shapes as one includes more and more of the water-insoluble block in the polymer chain. When the correct conditions are found for generating rod-shaped poly-MMA-CEM blocks, one crosslinks these blocks by light of the appropriate wavelength and intensity. Then the rods are fixed, and the water-soluble polymer block, poly-HEMA-AEM-ARS in this case, surrounds the rod. One then can obtain nanometer-scale rods bearing reactive amino groups. The dimensions of such rods are expected to be 1–30 nm in diameter and hundreds to thousands of nanometers long. Such rods should also function to reinforce polymer gel networks, just as methylated collagen is thought to reinforce the PEG network described elsewhere in this application.

Hedrick describes how to make PEG-PCL-PMMA segments of controlled size, but no reactive groups, and no linear chains with multiple pendant reactive groups. Nathan describes how to couple PEG and lysine to give a repeating polymer with reactive pendant chains (but no degradable ester links, and no addition of PCL and PMMA for strength). Abuchowski gives a method for making glutaryl-succinimidyl PEG. WO 99/17417, and references cited therein, describes PEG-polylactide-acrylate polymers to be polymerized by light and a free-radical process. These materials do not describe addition of PMMA for strength, nor do they mention pendant NHS or other groups for covalent (not free-radical driven) bonding.

Example 7

COH102/206/methylated collagen plus the fibrous fillers glass wool or Vicryl

Materials:
a. Methylated Collagen

Methylated collagen was prepared by a modification of the procedure of Miyata et al, U.S. Pat. No. 4,164,559. A dispersion (3% w/v) of bovine pepsinized reconstituted collagen in 0.02M sodium phosphate, 0.1 3M NaCl, pH 7.2 (prepared by the method of McPherson et al., Collagen Rel. Res. 5, 119–135, 1985) was extruded onto a glass surface in a thin layer and dried at room temperature. Methanolic HCl was prepared by adding 104 g of anhydrous sodium sulfate and 10.7 ml of conc. HCl to 1300 ml of anhydrous methanol and allowed to stand tightly capped for 2 days. The dried collagen was cut into 1×5 cm strips and added to the methanolic HCl (200 ml methanolic HCl: 1 g dry collagen) in a sealed vessel and gently shaken at 20 deg. C. for 3 days. The methanolic HCl was carefully decanted off and the collagen was filtered on a sintered glass funnel to remove traces of methanol. Complete methanol removal was completed under vacuum overnight. The methylated collagen was re-solubilized in distilled water, and the pH was adjusted to 4 to 6. The amount of water was calculated to achieve a final protein concentration of about 31 mg/ml. Samples of solubilized methylated collagen at lower protein concentrations were re-concentrated by brief lyophilization to remove water. Solubilized methylated collagen was a completely transparent material, free of fibers or opalescence, having a viscous, gel-like consistency. Preparations which still contained hazy or insoluble components (due to incomplete methylation of the collagen) performed poorly in adhesive formulations, producing gels that swelled too much and exhibited poor bond strength.

b. Adhesive Without Filler

Figure 9B:
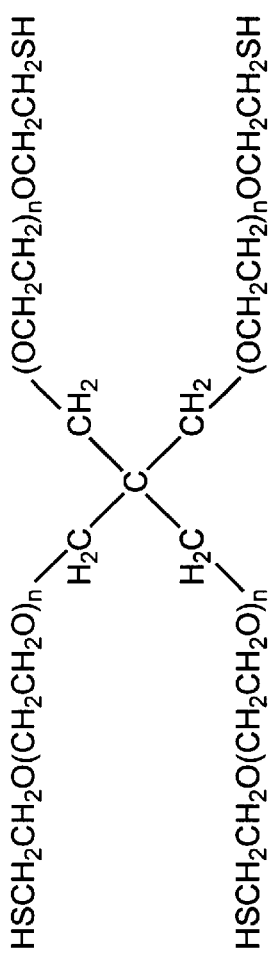

For 0.5 ml of adhesive, 50 mg of dry powdered COH102 (4-armed tetraglutaryl-succinimidyl polyethylene glycol, 10K; FIG. 9a) and 50 mg of dry powdered COH206 (4-armed tetra-thiol polyethylene glycol, 10K; FIG. 9b) were mixed with 400 mg of methylated collagen at 31 mg protein/ml, pH 4. Both PEG components dissolved in the aqueous solution of collagen, yielding a transparent, viscous fluid. The solution was spread on the tissue site with a spatula; it flowed very little under the force of gravity. To cure the adhesive, 20–50 $\mu$l of a buffer (either 134 mM sodium phosphate, 166 mM sodium carbonate, pH 8.9; or PC buffer, pH 9.6) was added to the surface. The buffer did not dilute the gel, but slowly soaked in. In 3–5 min, the surface of the gel was noticeably hardened.

For studies of bond strength under hydrated conditions, the gel plus substrate was allowed to cure for 20 min on the bench, then immersed in 50 mM sodium phosphate, 130 mM sodium chloride, pH 6.7, at 37 deg. C. for 2 hours or longer. Testing of bond strength was performed on a tensile apparatus.

c. Adhesive with Filler

Vicryl is a copolymer of glycolic acid and lactic acid (90:10) sold as an implantable mesh by Ethicon Corporation (Polyglactin 910; Sommerville, N.J.).

To the methylated collagen was added 19 mg of Vicryl threads 1–2 cm long which had been unraveled from implantable Vicryl mesh. In some cases, Vicryl fibers as short as 0.3 cm were also used. The threads and the viscous gel were blended, and then the PEG components were added, as described above. Application to the tissue site and curing were as above. Other fillers and their respective amounts added to 0.5 ml of adhesive were: glass wool, 9 mg; fibrous collagen (Semed F collagen, Kensey-Nash Corporation) 8 mg; Dexon S (poly glycolide lactide sutures, "4-0"), 10 pieces 1 cm long; elastin fibers (bovine neck ligament, 0.25 to 10 mm, Elastin Products Co., Inc, Owensville, Mo.), 40 mg; stainless steel fibers (Bekaert Fibre Technologies, Marietta, Ga.), 14–28 mg (Fibers were washed with water or 1N HCl to remove a polyvinylalcohol coating); polylactide/glycolide micro-particles, prepared from polylactide/glycolide (65:35, 40–75,000 mol. wt., Aldrich Chemical Co., micro-particles 2–4 diameter prepared by the method of Zheng, J., and Hornsby, P.J., Biotechnol. Progr. 15, 763–767 (1999), 25 mg.

d. Adhesive with Methylated Collagen Replaced by Another Agent

Various long-chain molecules were tested, such as hyaluronic acid (rooster comb, Sigma Chemical Co., St. Louis, Mo.), chitosan (Sigma), and polylysine (Sigma). For hyaluronic acid, the formula was: COH102, 50 mg, COH206, 50 mg, Vicryl, 14 mg, and 400 $\mu$l of hyaluronic acid, 2% (w/v) in water, pH adjusted to 4; for chitosan, the same formula, with 400 $\mu$l of 1% chitosan (w/v) in water, pH 4–5. For polylysine, COH102, 40 mg, COH206, 30 mg, dissolved together in 50 $\mu$l water; polylysine hydrobromide, 330K, 40 mg dissolved in 60 $\mu$l water; the two solutions were mixed together, and 7 mg Vicryl fibrils were added. In addition, polylactide/glycolide particles, prepared as above, were tested as a replacement for methylated collagen; 16.5 mg of particles were suspended in 300 $\mu$l of water and mixed with 50 mg COH102, 50 mg COH206, and 14 mg Vicryl. All gels were cured with pH 9.6 buffer overlay, as described above.

e. Adhesive Without Filler and Without Methylated Collagen

COH102 was dissolved in water at 20% (w/v); COH206 was dissolved at 20% in pH 8.9 buffer. The two solutions were rapidly mixed and extruded onto the site. Gelation occurred in ~40 sec.

Figure 10A:
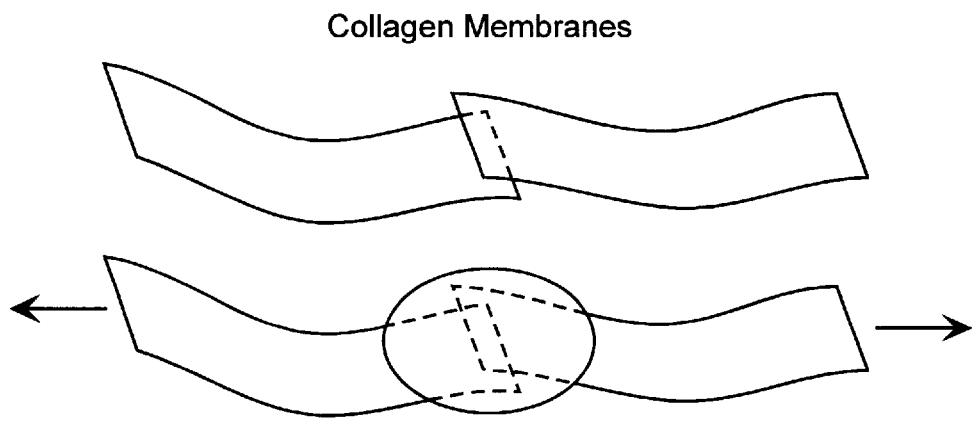
FIG. 10 depicts the types of devices that are useful for measuring tensile strength.
Figure 10B:
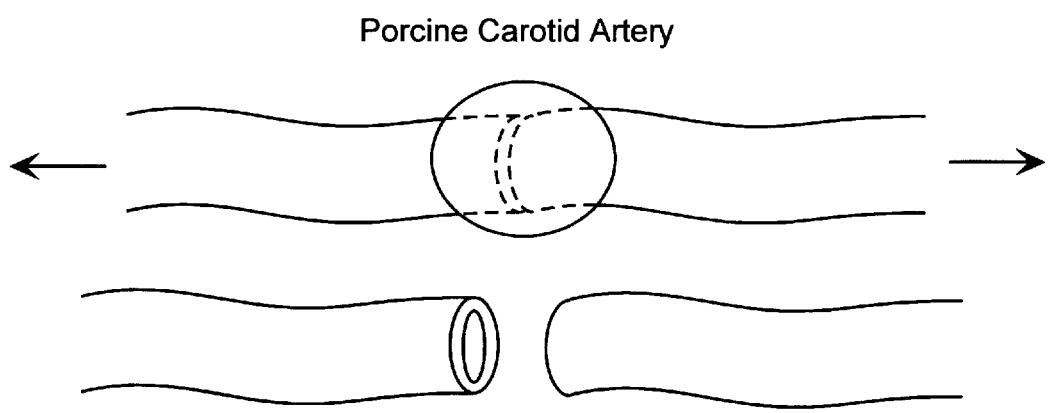
Figure 10C:
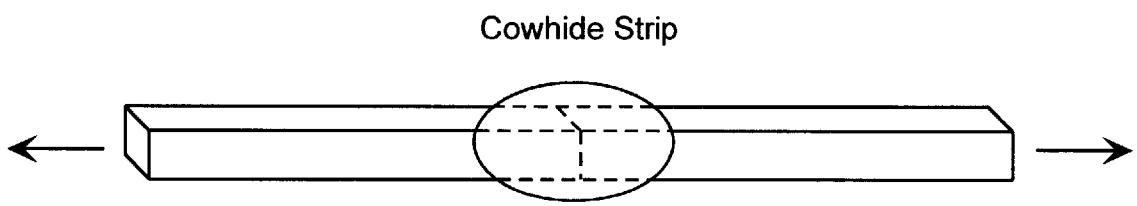

Mechanical Tests:

Bond strength of the adhesive formulations were applied to three types of tissue or tissue surrogates depicted in FIG. 10. Collagen membranes (FIG. 10a; sausage casings; The SausageMaker, Inc., Buffalo, N.Y.) were washed with isopropyl alcohol and water to remove lipid and salt impurities, and dried. Bonding of membranes with a 1–3 mm overlap and a 1 cm width was performed by spreading the adhesive over the top of the sheets. Adhesive was allowed to cure 20 min on the bench and then immersed for 30 min to 2 hours at 37° C. before pulling apart in an Instron model 4202 test apparatus (Canton, Mass.), using a 100N load cell. Bonding of porcine carotid arteries (10b, Pelfreeze, Rogers, Ark.) was also performed in an end-to-end geometry. Cut carotid artery segments were abutted (4–6 mm diameter) and spread with adhesive; no stay sutures were applied. Incubation and testing were the same as described for the collagen membranes.

For bonding of cowhide strips (10c), de-haired calf skin pieces were purchased from Spear Products, Inc., Quakertown, Pa. Pieces were nearly uniform in thickness, 2–3 mm. Strips 0.4 cm wide were cut from the hide pieces, using a single-edged razor blade. Cut strips were abutted end to end and bonded by spreading 0.25 ml of "CT003" adhesive or a few drops of cyanoacrylate. Incubation and testing were the same as described for the collagen membranes. Table 8 below shows that COH102/COH206/methylated collagen, when filled with glass wool (Formula c), was superior in bonding strength to unfilled Formulas a and b when tested on collagen membranes. In fact, the bonding strength was comparable to that obtained with a commercial cyanoacrylate adhesive (Table 9). A medical grade cyanoacrylate (Dermabond) formed even stronger bonds with collagen membranes (5.2±1.9 N force for 7 determinations).

TABLE 8

Bonding performance with and without methylated collagen and a fibrous filler

| Formula | Bond Strength (N Force) | n |
|---|---|---|
| COH102/206 (20%) | 1.6 ± 1.1 | 3 |
| COH102/206/methylated collagen | 1.7 ± 1.0 | 4 |
| COH102/206/methylated collagen/glass wool | >2.8 ± 0.6* | 6 |

Collagen membrane tore, but sealant bond was still intact

TABLE 9

Bond strength of cyanoacrylate (Krazy Glue, Elmer's Products) on three different tissue substrates

| Substrate | Bond Strength (N Force) |
|---|---|
| Cowhide strips | 10.9, 16.2 |
| Porcine carotid artery | 2.0, 3.8 |
| Collagen membrane | 3.0 ± 1.0 (n = 5) |

Table 10 below presents data on the addition of a different filler, Vicryl threads, to the COH102/206/methylated collagen. With substrates such as cowhide or carotid artery, the substrate did not tear, and the bond strength values were representative for the strength of the adhesive bond itself. Typically these bonds failed adhesively, that is, the tensile strength of the adhesive gel itself remained intact and was not the limiting factor. The bond strengths observed in Saline at 37° C. again were comparable to those seen with cyanoacrylate for bonding the same set of tissue substrates (Table 9).

TABLE 10

Bond strength of COH102/206/methylated collagen with Vicryl threads as a filler on three different tissue substrates.

| Incubation Time (Hrs.) | Bond Strength (N Force) | Substrate* |
|---|---|---|
| 2 | 6.6, 5.6 | Cowhide |
| 17 | 6.3, 5.5 | Cowhide |
| 2 | 4.3, 2.2, 2.8, 5.1 | Porcine Carotid Artery |
| 2 | >5.9, 3.9 | Collagen Membrane |

*cowhide strips, 0.5 cm wide, porcine carotid artery, 0.3–0.5 cm diameter, collagen membrane: sausage casing, 0.2 mm thick, 1 cm width.

Effect of Different Fillers

Table 11 presents results of various filler materials. Testing was performed on cowhide strips, immersed for 2 hours in saline at 37° C. It appeared that filamentous materials were more effective than spheroidal particles. Bonding of the filler to the gel is very important for improvement of strength. Collagen-polyethylene glycol filaments were waxy and did not adhere to the gel; thus, despite their high aspect ratios, they were not effective fillers.

TABLE 11

Effect of different fillers on bond strength of COH102/206/methylated collagen

| Material | Bond Strength (N Force) |
|---|---|
| Vicryl | 4.7, 7.4 |
| Vicryl, washed with ethanol | 7.2, 7.8 |
| Vicryl, treated with ethanol, then washed with 30% hydrogen peroxide | 8.3, 9.1 |
| Surgical silk sutures 1–2 cm long, 30-50 u diameter | 2.5, 3.8 |
| Surgical silk sutures, unraveled to finer threads, washed with chloroform | 5.0, 6.5 |
| Fibrous collagen (Semed F, Kensy-Nash) adjusted to pH 4; 0.5 to 1 mm long, ~50 u diameter | 1.3, 2.8 |
| Gelatin particles, cross-linked by heat, 100 u diameter, polygonal | 0.6, 0.8 |
| Hydroxyapatite particles, 0.5 to 1 mm diam. polygonal | 0.7 |
| Collagen-polyethylene glycol conjugate filament 50 u diameter, 1 cm long | 0.8, 1.7 |
| Stainless steel fibers 8 u diameter, 4 mm long | 4.8, 6.9 |
| Elastin fibers 0.25 to 10 mm long | 3.9, 4.0 |
| Polylactide/glycolide particles 2 u diameter | 1.1, 1.1 |

Effect of Replacing Methylated Collagen with other Polymeric Molecules

Table 12 shows that none of the tested materials gave bond strengths comparable to the formula containing methylated collagen

TABLE 12

Replacement of Methylated Collagen by Other Molecules

| Material | Bond Strength (N force) |
|---|---|
| hyaluronic acid | 1.2, 1.3 |
| chitosan | 2.1, 1.7 |
| polylysine | 2.0 |
| polylactide/glycolide particles, 2–4 u | 0.6, 1.1 |

Effect of Cross-linking Bond.

Figure 11:
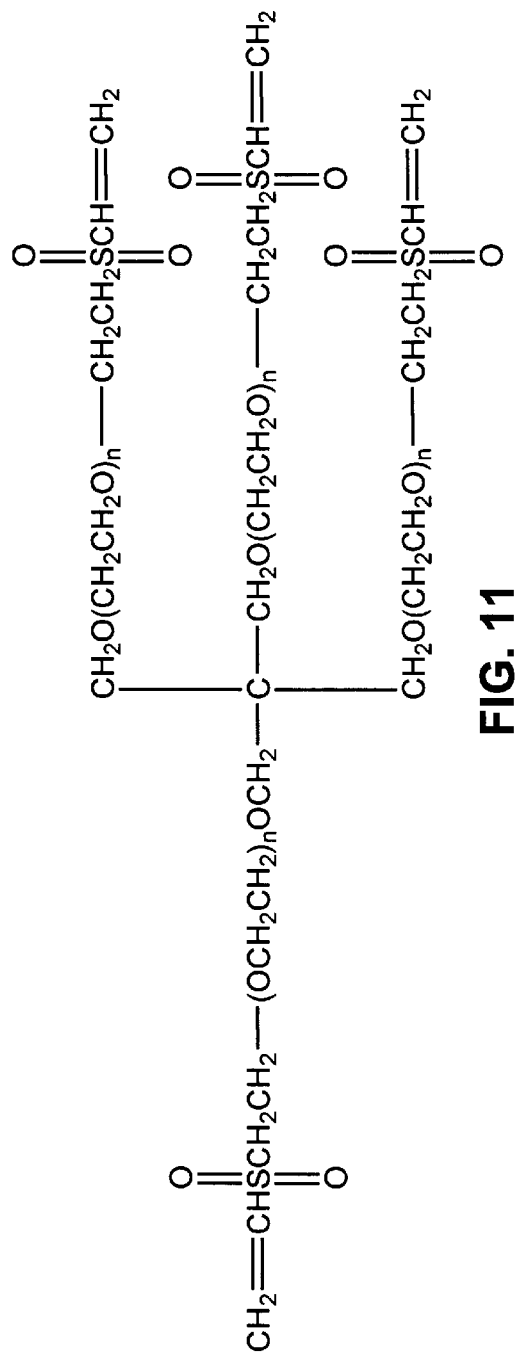
FIG. 11 depicts the structure of a 4-arm vinyl sulfone derivative of PEG.
Figure 12:
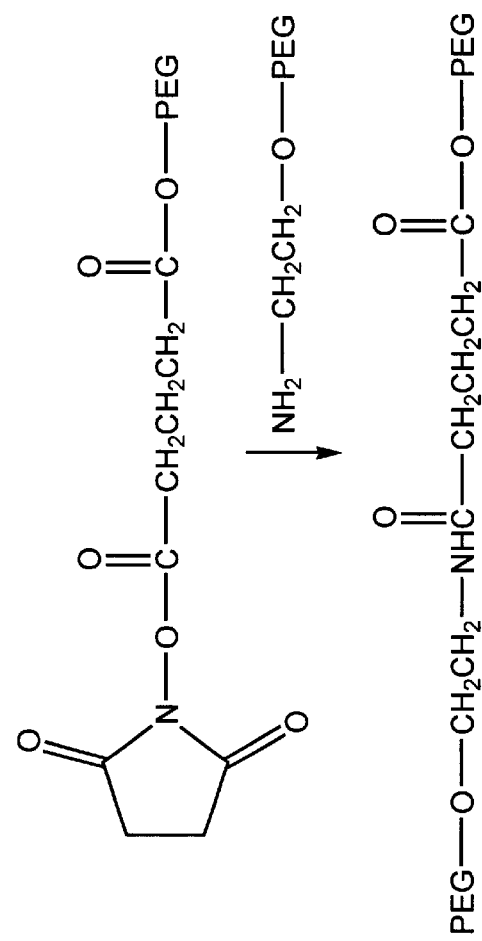
FIG. 12 depicts the formation of an amide and a carbxyl ester linked PEG conjugate from succinimidyl-glutaryl-PEG plus amino-PEG.

Table 13 below shows that when the gel was formed from other types of cross-linking reactions, the adhesion and bond strength was affected when tested on cowhides after incubation at 37° C. Material 1 was formed from COH206 and hydrogen peroxide, which oxidizes adjacent sulfhydryl groups to a disulfide bond. A gel forms rapidly, and the gel can be supplemented with methylated collagen and Vicryl; however, after several hours in saline buffer, the gel becomes very weak; the Vicryl fibers are easily pulled out. Material 2 utilized the reaction of sulfhydryl groups from COH206 with the double bond of a 4-arm vinyl sulfone derivative of PEG (10K, Shearwater Polymers; FIG. 11). The presumed reaction, a Michael-type addition, formed a thio-ether bond. Such gels had adequate tensile strength but poor adhesion to the cowhide after incubation in saline. Materials 3 and 4 contained COH204 (4-armed, tetra-functional amino PEG, 10K, Shearwater Polymers); the amino functionality presumably reacted with the succinimidyl ester of COH102 to form an amide linkage (FIG. 12). These gels were comparable in performance to those formed from COH102 and COH206. (For proper reaction in the presence of methylated collagen, the COH204 had to be titrated to pH 2–4 during the mixing of reagents; on addition of curing buffer, its pH was increased, permitting the reaction of the amino group). It appeared that the presence of the succinimidyl ester was important for achieving the highest adhesion to the tissue substrate and for good tensile strength of the gel. Other groups that react with amines, such as aldehydes (aldehydes conjugated to multi-armed PEG), are also anticipated to be effective adhesive-forming reagents.

TABLE 13

Bond Strengths of Various Functionalized PEGs Filled with Vicryl Threads

| Material | Incubation Time (Hrs.) | Bond strength (N force) |
|---|---|---|
| COH206/Methylated Collagen/Vicryl/$H_2O_2$ | 17 | 0.32, 0.20 |
| COH206/4arm vinyl 2 sulfone PEG/Metylated Collagen/Vicryl threads | 2 | 2.2, 1.5 |
| COH102/206/204/ Methylated Collagen/ Vicryl threads | 2 | 6.4 |
| COH102/204/ Methylated collagen/ Vicryl threads | 4 | 3.6, 6.4 |
| COH102/206/ Methylated collagen/ Vicryl threads | 2 | 6.6, 5.6 |

Persistence of the Bond Under Hydrated Conditions.

Table 14 shows that the adhesives formed from COH102, COH206, and also COH204 form bonds using cowhide that persist for long times immersed in saline buffer at 37 deg. C.

Figure 13:
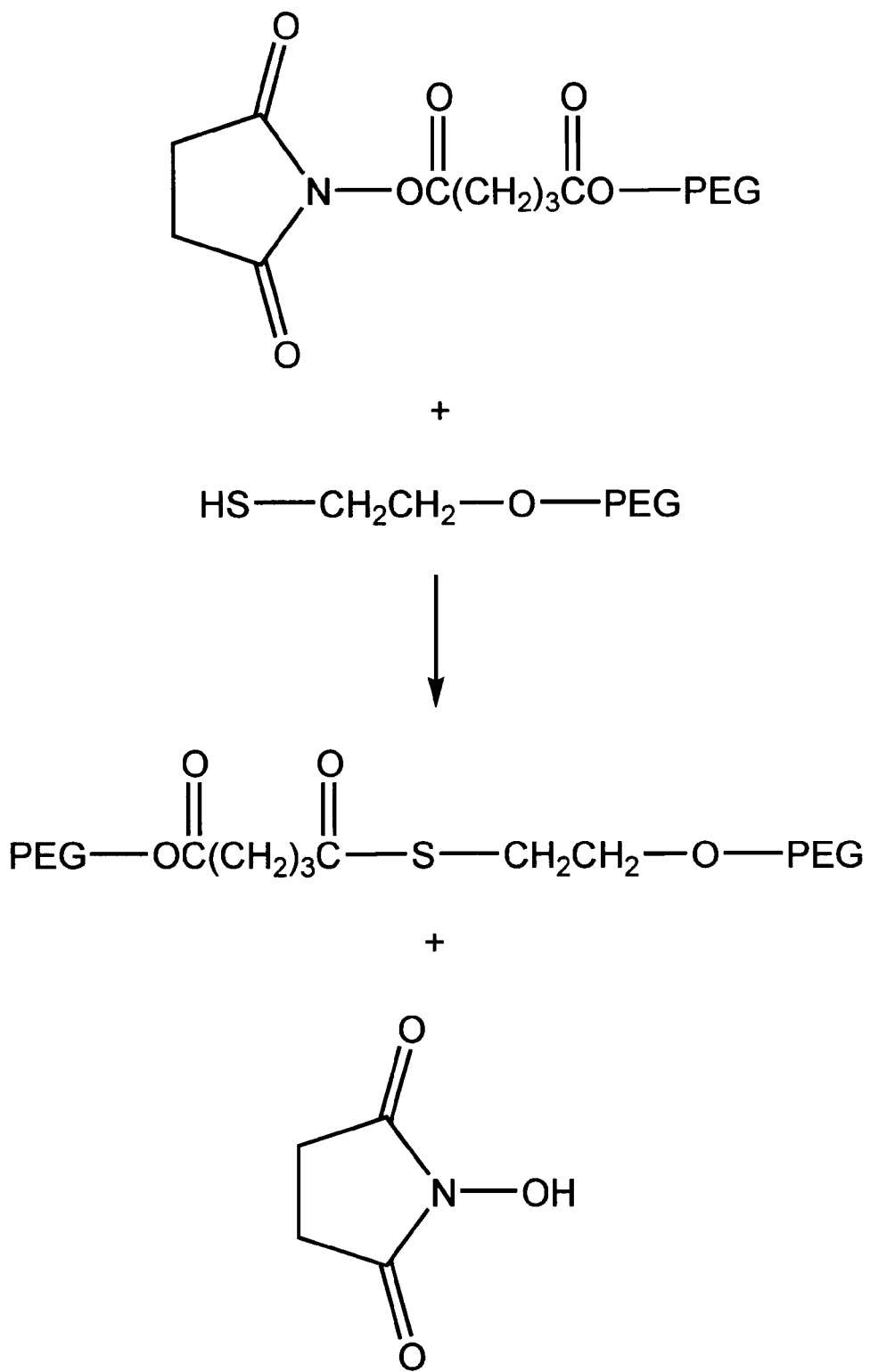
FIG. 13 depicts the formation of a thioester linked PEG conjugate from succinimidyl-PEG and thiol-PEG.

Such stringent hydrated conditions simulate the in vivo environment. Bond weakening was observed after more than 100 hours of hydration. The weakening of bond strength was thought to be due to hydrolysis of carboxyl-ester and thio-ester (FIG. 13) network linkages. COH102 is a glutaryl-succinimidyl ester; even after reaction with the terminal carboxyl of the succinimidyl ester, there remains a carboxyl ester linking the glutaryl moiety to the main PEG chain; this bond, as well as the thio-ester bond, could hydrolyze.

TABLE 14

Bond Performance Under Long Hydration Times

| Material | Incubation Time (Hrs.) | Bond Strength (N force) |
|---|---|---|
| COH102/206/204/ | 2 | 6.4 |
| Methylated collagen/ | 66 | 2.6, 4.1 |
| Vicryl threads | 70 | 3.0 |
| | 137 | 0.70, 2.6 |
| | 140 | 1.1, 0.4 |
| COH102/204/ | 4 | 3.6, 6.4 |
| Methylated collagen/ | 64 | 7.0, 5.1 |
| Vicryl threads | 136 | 3.8, 2.7 |
| | 234 | 2.7, 1.7 |
| COH102/206/ | 2 | 6.6, 5.6 |
| Methylated collagen/ | 17 | 6.3, 5.5 |
| Vicryl threads | 69 | 0.63, 0.90, 3.4, 5.4 |
| | 93 | 2.4, 5.4 |
| | 140 | 3.2, 2.9 |
| | 235 | >2.4, 3.7 |

Related Formulas with Lower Molecular Weight Compounds Bearing Succinimidyl Ester and Amino or Thiol Reactive Groups.

Table 15 presents bond strengths on cowhide strips of lower molecular weight PEG derivatives as adhesives, again supplemented with methylated collagen and Vicryl. GLYC-20HS is a tri-functional succinimidyl-succinate of a 3-armed PEG built from a glycerol core, 2600 mol. wt., NOF Corporation, Japan. COH201 is a tetra-amino, 4-armed PEG, 2000 mol. wt., Shearwater Polymers. The polymers were Vicryl filling appeared to have a small effect on bond strength. The following proportions were used: Methylated Collagen, 500 µl (22 mg/ml in water 2707-30B); GLYC-20HS, 48 mg; COH201, 60 µl of 60% solution in water, titrated to pH 1–2 with 6M HCl; Vicryl threads, 26 mg.

TABLE 15

Low Molecular Weight Analogues to COH102 and COH206

| Materials | Incubation Time (Hrs.) | Bond strength (N force) |
|---|---|---|
| GLYC-20HS/ COH201/Methyated Collagen | 2 | 2.3, 0.64 |
| GLYC-20HS/ COH201/Methylated Collagen/Vicryl threads | 5 | 2.3, 3.3 |

Burst Tests on Collagen Disks and on Slit Defects in Carotid Arteries

Performance of adhesives intended for use in surgical applications is often measured by their ability to seal fluid leaks. Two types of leaks, or fluid pressure tests were employed:

a. The Burst test on a Collagen Disk

Figure 15:
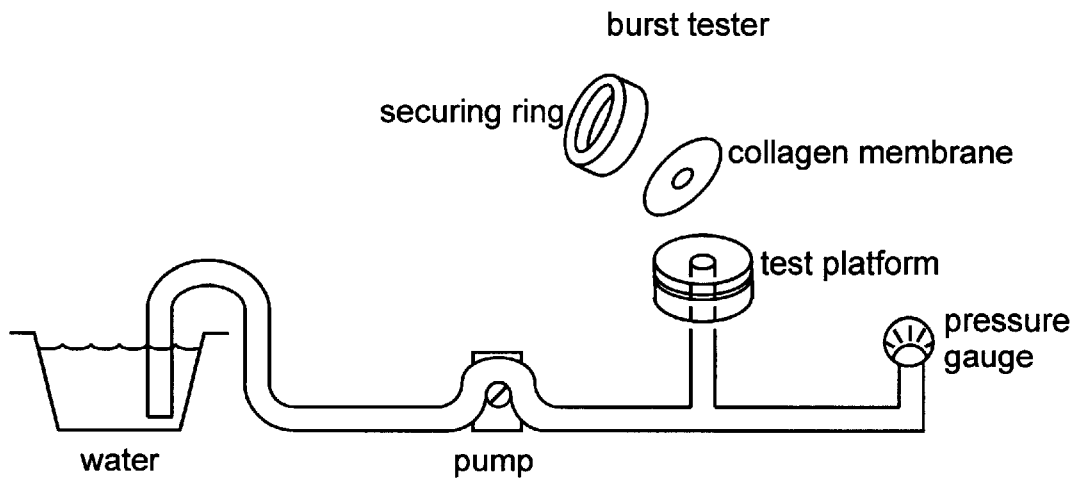
FIG. 15 depicts a device that is useful to test burst strength of a collagen membrane.

Using the device depicted in FIG. 15, collagen mat was mounted on a brass platform and secured with a second brass ring threaded to the first. The lower brass platform was perforated and connected to a line filled with water. Water was driven by a syringe pump at 5 ml/min. A shunt line led to a pressure gauge. The test collagen mat was also perforated (2 mm diameter hole). The adhesive preparation (approx. 0.5 ml) was applied to the mat, covering the perforation. The adhesive was allowed to cure 3 min (or longer, if necessary to effect cure to a firm rubber), then water pressure was applied. The pressure necessary to rupture the seal was recorded. For cyanoacrylate, a small (4×4 mm) piece of collagen mat was glued to the lower perforated mat.

b. Slit Defect on Carotid Artery

Figure 16:
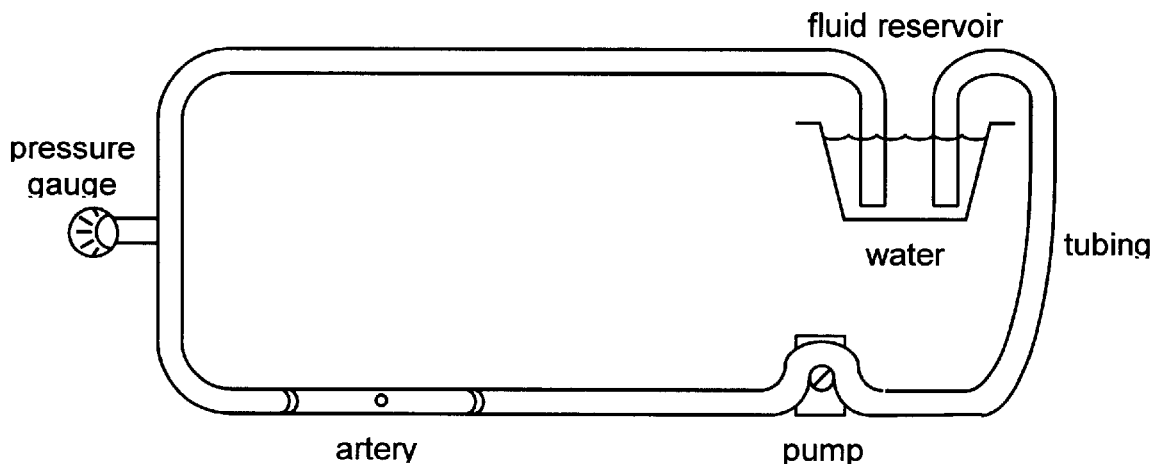
FIG. 16 depicts a device (a pressurized carotid artery model) that is useful to test burst strength of a repaired artery slit defect.

The pressurized carotid artery model is illustrated in FIG. 16. A porcine artery (Pel Freeze Biologicals, Rogers, Ark.) was connected to a water line. Water was driven by a peristaltic pump. The end of the line had a flow restricter placed on it so that pressures up to 10 psi and more could be imposed on the line by increasing the pump speed. First the intact artery was placed in the system and subjected to water pressure, to assure that it would sustain desired pressures without leaking. Sections of artery devoid of side branches were preferred; leaking branches sometimes were clamped off to stop leaks. Slits approximately 2 mm long were cut transversely in the artery at four sites on a circumference (FIG. 16). The cut artery then simulated an anastomosis to which stay sutures had been applied. The cut sites were then glued all around in an attempt to seal them. Buffer (134 mM sodium acid phospate and 166 mM sodium carbonate, pH 8.9) was applied to the artery tissue just before the glue was applied. The glue mass was further irrigated with a few drops of this buffer to cure the gel. After 8 min cure time, the glued joint was subjected to water pressure. Pressure was increased at 1 psi increments and held at each pressure for 1 minute before increasing further. A leak was scored as positive if it was dripping faster than 1 drop every 10 seconds.

Table 16 shows the burst strengths of COH102/206/ methylated collagen/Vicryl on holes of varying diameters (on collagen membranes at 8 min cure time; cured with pH 8.9 buffer; 0.5 ml sample spread over hole with spatula). A hole with a diameter of 5 mm is the largest defect one might contemplate in a surgical application, since stay sutures would be used to close the largest defects, and the largest interval between such sutures was estimated to be 5 mm. Even with such large holes, the adhesive was able to sustain pressures near or above the maximum expected in hypertensive patients, i.e., 4 psi. The third data entry emphasizes the need to have good gel curing at the interface of gel and collagen disk. The addition of curing buffer to this surface prior to application improves the short-term bonding.

TABLE 16

Burst Strength of COH102/206/methylated collagen/Vicryl

| Diameter of Orifice (mm) | Burst Pressure (PSI)* |
|---|---|
| 2 | >3.0, 7.4, 4.6 |
| 5 | 3.1, 5.5, 5.3 |
| 5 | 1.0+ |

*1 PSI = 0.68 N/CM$^2$ = 51 mm Hg
4 PSI = 2.7 N/CM$^2$ = 204 m Hg
+Membrane not pre-treated with a drop of pH 8.9 buffer Table 17 presents data on closing large slit defects in carotid arteries (4×2 mm slits cut on 4–6 mm diameter artery). The COH102/206/methylated collagen/Vicryl formula was comparable to cyanoacrylate in performance. It should be noted that poorer results are seen on thinner arteries that stretch more under pressure.

TABLE 17

Burst Strength Test on Porcine Carotid Artery

| Material | Burst Pressure (PSI) | Cure Time (min) |
|---|---|---|
| COH102/206/ Methylated Collagen/ Vicryl | 4.3 ± 2.0 (n = 5) 8.0 ± 4.0 (n = 3) | 8 30 |
| Cyanoacrylate (Elmer's Products) | 2.7 ± 3.6 (n = 6) | 8 |
| Cyanoacrylate (Dermabond) | 5.5 ± 5.2 (n = 4) | 8 |

Example 8

Figure 17:
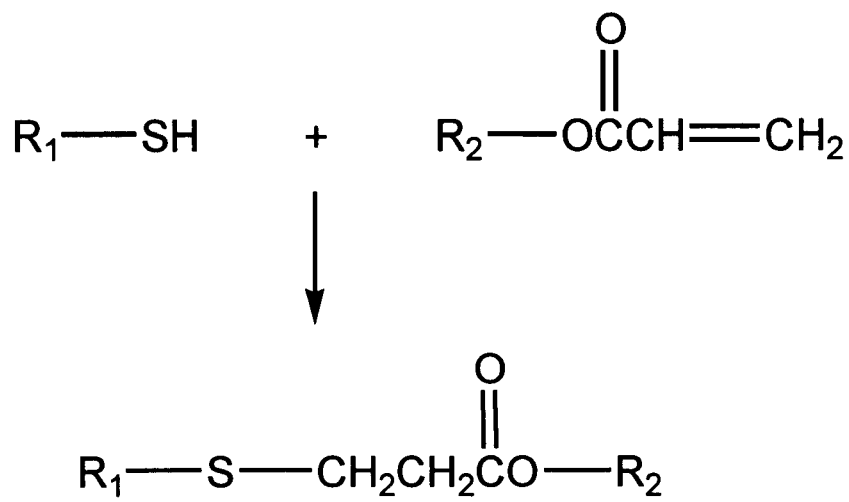
FIG. 17 depicts the formation of a thioether linkage from the reaction of thiol with acrylate.
Figure 18:
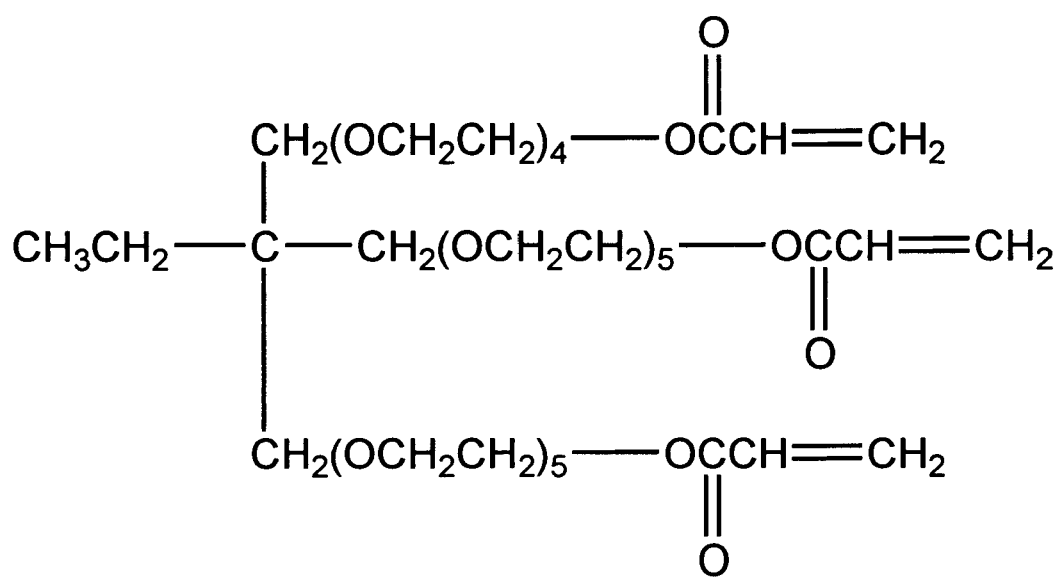
FIG. 18 depicts the structure of TPETA (tri-methylol propane ethoxylate tri-acrylate).
Figure 19:
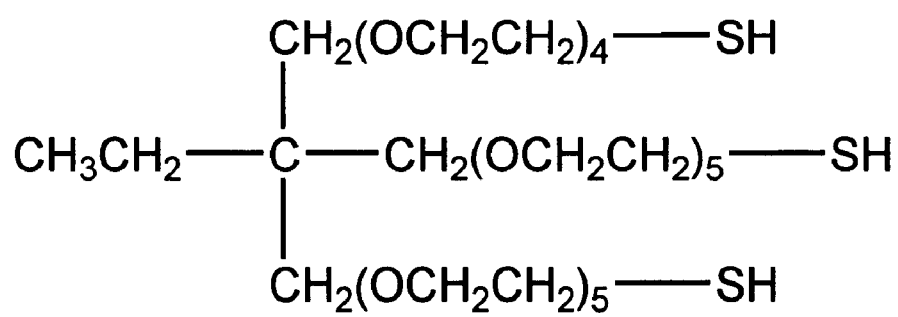
FIG. 19 depicts the structure of TMPE-SH (tri-methylol propane ethoxylate tri-thiol).

Derivatives of Penta-erythritol and Tri-methylol Propane functionalized with Thiol and Acrylate, Plus Fillers Such as Vicryl This class of adhesives was prepared from neat liquid reagents (no aqueous buffer added). The coupling reaction involved the addition of thiol groups into the activated double bond of acrylate is shown in FIG. 17. Table 19 below presents bond strength data on the reactive pair TPETA (tri-methylol propane ethoxylate tri-acrylate, mol. wt. 912, Aldrich Chemical Co.; FIG. 18) and TMPE-SH (tri-methylol-propane ethoxylate tri-thiol, mol. wt. 1140 (FIG. 19), synthesized from trimethylol propane ethoxylate, mol. wt. 1100, Aldrich Chemical Co.) To drive the reaction, a base was needed to convert the thiol to a thiolate anion. T403, a tri-amino 3-armed propylene oxide, 970 mol. wt., was used (Texaco Chemical Co., FIG. 2c.) The gel formed was sufficiently strong that only Vicryl was added as a filler. Methylated collagen was not added. (It was unlikely that methylated collagen, dissolved in water, would have remained in solution with the neat liquid TPETA and TMPE). The formulation was as follows:

TABLE 18

TPETA/TMPE-SH/T403/Vicryl

| Amounts | Mmoles reactive groups |
|---|---|
| 160 mg TPETA | 0.53 |
| 200 mg TMPE-SH | 0.53 |
| 10 μl T403 | 0.03 |
| 15 mg Vicryl threads, 1–2 cm length | |

TMPE-SH and T403 were mixed together, followed by addition of Vicryl threads, and finally the TPETA was added and mixed with the other components. The mixture was spread on wet test substrates with a spatula, as described above. The mixture became tacky in about 3 min, and was a firm gel in 5 min. Thereafter, the test mixture was immersed in saline as described above after 20 min. Gel time was freely controllable by the amount of T403 added.

Table 19 shows that bonding was achieved to all three tissue substrates, but the bond strength was lower than for the COH102/206 formulations. The bond failure was always adhesive—these gels exhibited high tensile strength but did not adhere well to tissue. However, in certain clinical applications, strong adherence to tissues is not necessary. This characteristic was particularly evident on the collagen membrane. The chemical coupling reaction apparently does not provide a suitable mechanism for covalent bonding to tissue, such as is the case with COH102, in which the succinimidyl ester can, in principle, react with amino groups on tissue. Free sulfhydryl groups on tissue proteins could react with the acrylate group of TPETA, but such groups are relatively rare on proteins.

TABLE 19

Bond strength of TPETA/TMPE-SH/VICRYL/T403 on three tissue substrates.

| Incubation Time (Hrs) | Bond Strength (N Force) | Substrate* |
|---|---|---|
| 2 | 3.3, 6.0 | Cowhide* |
| 18 | 3.7, 2.9 | Cowhide |
| 2 | 1.7, 2.0 | Porcine Carotid Artery |
| 2 | 0.7, 0.5 | Collagen Membrane |

*cowhide strips, 0.5 cm wide, porcine carotid artery, 0.3–0.5 cm diameter, collagen membrane: sausage casing, 0.2 mm thick, 1 cm width.

Table 20 shows that TPETA/TMPESH formulations, although they exhibited only modest bonding to cowhide strips during long immersion in physiological saline at 37° C., nevertheless exhibit persistent bonds after immersion in saline. This is thought to be due to the relative stability of the thio-ether bond, relative to bonds present in the COH102/206 gels. The material mol. ratios used were 0.59:0.52:0.031, 15 mg for TPETA:TMPE-SH:T403:Vicryl, mg/0.39 ml.

TABLE 20

Performance of TPETA/TMPE-SH/T403/Vicryl as an adhesive

| Incubation Time (Hrs) | Bond strength (N force) |
|---|---|
| 2 | 3.3, 6.0 |
| 18 | 3.7, 2.9 |
| 66 | 2.8, 3.3 |
| 260 | 2.5, 3.1 |

Example 9

Tensile Strength of Hydrated Adhesive Materials

The adhesive formulations described here usually fail adhesively—their cohesive strength appears not to be the limiting factor. The data below compare the tensile strengths of the adhesive itself to other adhesives and hydrogels. Measurement of tensile strength after 2 hour immersion in saline at 37° C.

The adhesive was formed into a roughly cylindrical shape and allowed to cure on a polystyrene weighing boat for approximately 20 min at room temperature. Then the sample was immersed in water for 2–2½ hours at 37° C. The sample was removed from the water, blotted, and tape was affixed to either end with cyanoacrylate glue. The sample was then mounted in an Instron tensile tester, gripped at either end by the tape, and extended to failure. The ultimate tensile strength in N/cm was noted, relative to the cross-sectional area of the sample at the break point. In some cases stress-strain curves were computed using $\Delta L/L_O$ as the strain, where $\Delta L = L - L_O$, L is the sample length at time t, and $L_O$ is the original sample length. To prepare a control sample consisting of cyanoacrylate alone, cyanoacrylate was streaked onto beef liver. After approximately 20 minutes, the cyanoacrylate had cured to a strip. It was peeled off the liver (which is an extremely fragile tissue), and the residual liver particles were removed. A clean, relatively uniformly cured cyanoacrylate polymer strip was thus obtained.

Figure 20:
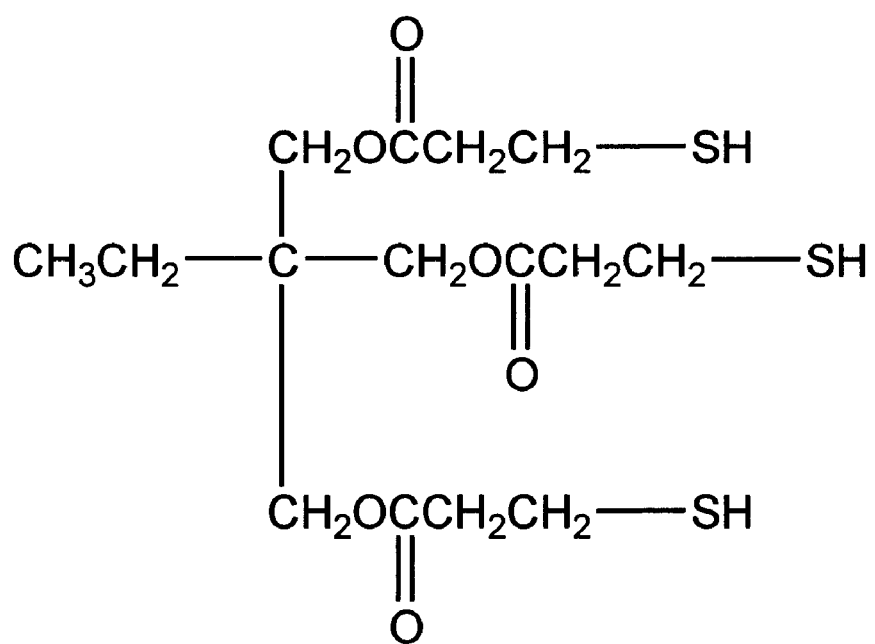
FIG. 20 depicts the structure of TPT-SH (tri-methylol propane tris(3-mercapto-propionate).

The data shown in Table 21 show that the adhesives containing a tensile strength enhancer exhibit higher tensile strength than hydrogels without such an enhancer. The acrylate-thiol class of adhesives (such as TPT-SH: trimethylol propane tris (3-mercaptopropionate), FIG. 20) containing Vicryl had higher tensile strengths than cyanoacrylate alone. Formulations without a tensile strength enhancer had tensile strengths of approximately 8 to 20 N/cm$^2$. COH102/206 (20%) is a simple hydrogel—it had a much lower tensile strength than the corresponding formulation containing methylated collagen and Vicryl. Measurements were taken after 2 hr immersion in saline at 37° C.

TABLE 21

Tensile Strength of Selected Adhesives

| Material | Tensile Strength (N/cm$^2$) |
| --- | --- |
| COH102/206/ Methylated Collagen/ Vicryl | 84 ± 21 (n = 5) |
| TPETA/TPT-SH/ GdMA/T403/Vicryl[1] | 310 ± 160 (n = 2) |
| Cyanoacrylate (Krazy glue, Elmer's Products) | 200 ± 7 (n = 2) |
| COH102/206 (20%) | 7 ± 5 (n = 3) |
| Gelatin-PEG-di-acrylate[2] | 5–16 |
| pHEMA[3] | 3 |

Figure 21:
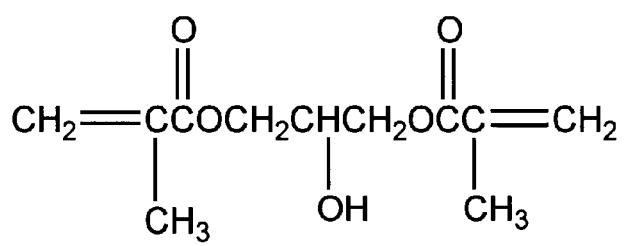
FIG. 21 depicts the structure of glycerol-di-methacrylate.
Figure 22:
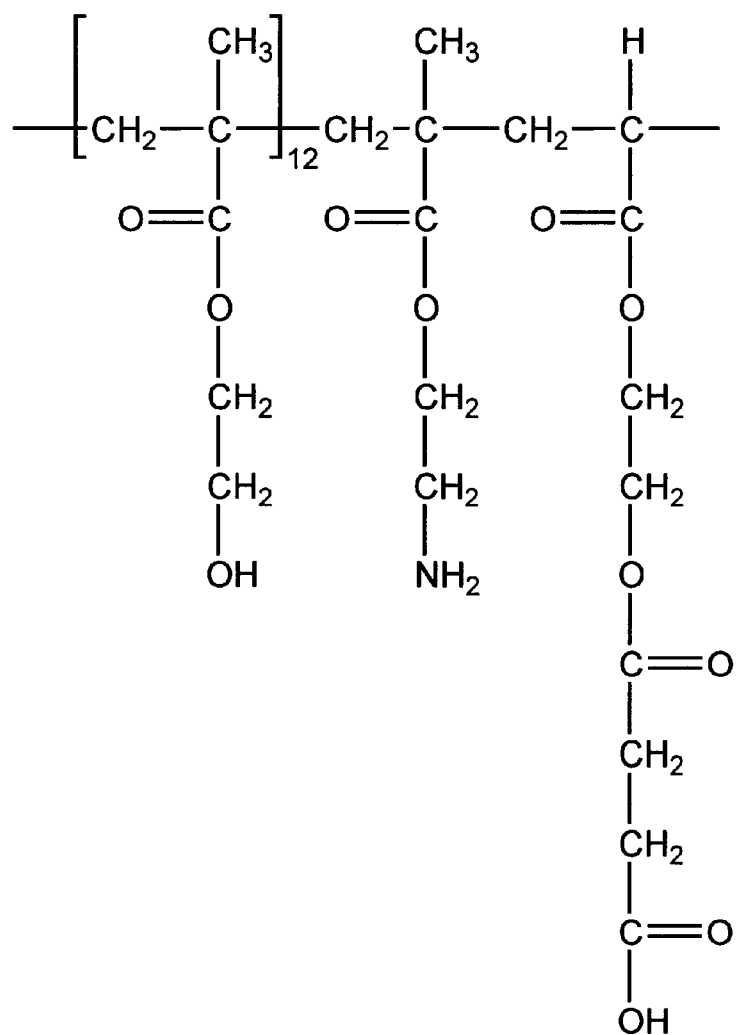
FIG. 22 depicts the structure of poly-hydroxyethymethacrylate-co-aminoethyl methacrylate-co-mono-2-(acryloxy) ethyl succinate.

[1]TPT-SH: trimethylol propane tris (3-mercaptopropionate) (FIG. 20), mol. wt. 400, Aldrich; GdMA: glycerol di-methacrylate, Aldrich (FIG. 21)
[2]Nakayama, Y., and Matsuda, T., "Photocurable surgical tissue adhesive glues composed of photoreactive gelatin and poly(ethylene glycol) diacrylate", J. Biomed. Biomat. Res. (Appl. Biomater.) 48, 511–521 (1999).
[3]pHEMA: poly hydroxymethacrylate; Santin, M., Huang, S. J., Iannace, S., Ambrosio, L., Nicolais, L., and Peluso, G., "Synthesis and characterization of a new interpenetrated poly(2-hydroxy ethylmethacrylate)-gelatin composite polymer", Biomaterials 17, 1459–1467.

Example 10

Linear Copolymers with Pendant Reactive Groups.

The objective of this experiment was to find a means to synthesize linear chain polymers with pendant reactive groups as shown in FIG. 1. A further objective was to be able to insert into the linear polymer chain, not only pendant reactive groups, but also monomeric subunits or polymer blocks which could impart toughness to the gels formed from the polymer. As such, this experiment is an extension of Example 6 above.

Figure 14:
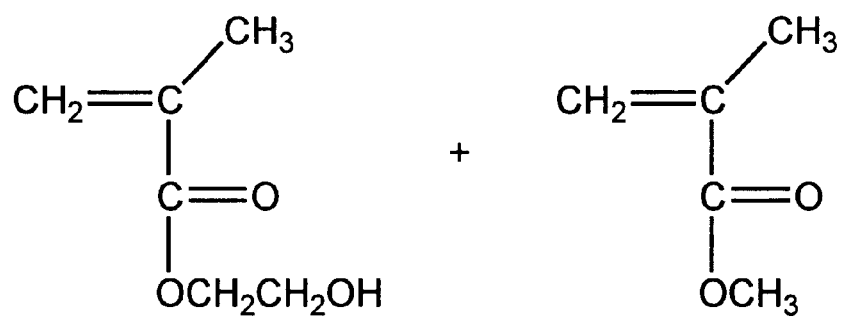
FIG. 14 depicts the structures of HEMA (hydroxy-ethyl-methacrylate), MMA (methyl-methacrylate), mono-2-(acryloxy)ethyl succinate and 2-amino-ethyl methacrylate.
Figure 14:
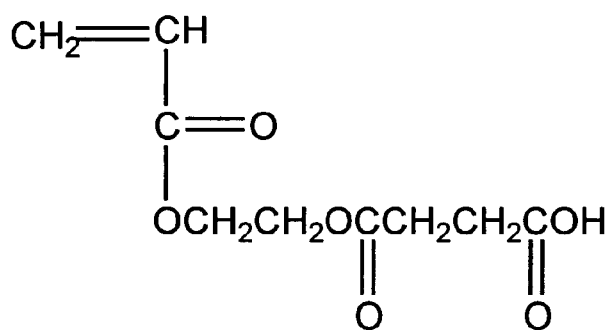
Figure 14:
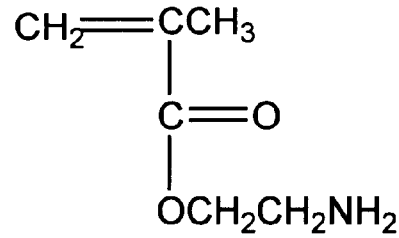

All the polymers prepared were of the poly-acrylate/methacrylate family. Following a procedure outlined in Sun, Y-M, et al, "Composite poly(2-hydroxyethyl methacrylate) membranes as rate-controlling barriers for transdermal applications", Biomaterials 18, 527–533,1997, linear polymers were prepared. The monomers included in the polymerization were HEMA (hydroxy-ethyl-methacrylate), MMA (methyl methacrylate), ARS (mono-2(acryloxy)ethyl succinate), and AEM (2-amino-ethyl-methacrylate) (FIG. 14).

Polymerization to form Poly-HEMA with carboxyl and amino side chains was carried out for 4 hrs at 75° C. with the following ingredients: HEMA, 1260 μl; ARS, 240 μl; AEM, 348 mg; azobis-isobutyro-nitrile, 54 mg; and dry ethanol, 34 ml. Precipitation was carried out with dry petrolium ether.

The polymerization was initiated with azobis-isobutyro-nitrile in dry ethanol, with vigorous stirring. AEM, which is poorly soluble in ethanol, was first dissolved in water (50% w/v), the solution adjusted to pH 2–4 with HCl, and added to the solution of the other constituents in ethanol. The entire reaction was flushed with nitrogen and conducted in a screw-cap bottle in a water bath. Free-radical inhibitors in HEMA and MMA were removed by passing these reagents through a column of aluminum oxide 90 (Active neutral, activity 1, 70–230 mesh, EM Science, Gibbstown, New Jersey) just before addition to the reaction mixture. After 4 hours at 70–80° C., the solution was cooled, filtered to remove insoluble AEM and other particulates, and the polymer was precipitated by adding 10 ml of petroleum ether. The polymer coagulated on the surface of the glass beaker, and the spent ethanol solution was decanted off. The polymer was dried under vacuum for several days.

Table 22 shows that polymers apparently were obtained, and for the first two samples in the table, gels were rapidly formed with COH102, suggesting the presence of AEM moieties in the polymer chain. In the case of earlier polymer preparations, the relative amount of amino and carboxyl functionality on the polymer was estimated from a titration curve. Approximately 1 AEM subunit and 2 ARS subunits were present for each 20 HEMA units along the chain. See FIG. 23.

None of the polymer gels which were formed were tougher than hydrogels formed from COH102 and COH206 alone. Co-polymers high in MMA were chalky and crumbled readily. MMA was originally chosen because pMMA itself is a tough, water-insoluble polymer. Accordingly, these classes of polymer chains with pendant reactive groups are apparently not suitable for use in the present invention. Further modification of the ratio of these acrylate/methacrylate monomers, or introduction of other monomers of the acrylate family, may result in a polymer with the desired properties, and such optimization studies can easily be carried out using the teachings herein.

TABLE 22

Properties of poly-acrylate/methacrylate polymers synthesized

| HEMA:MMA ratio | Gelation (+ or −)[1] | Soluble (Y or N) | Mol. Wt. (Daltons)[2] |
| --- | --- | --- | --- |
| 100:0 | + | Y | 880 |
| 80:20 | + | N | 1300 |
| 50:50 | − | N | 4500 |

[1]Approximately 50% (w/v) solutions or dispersions of the polymer in pH 9.6 buffer (described above) were mixed with a 50% (w/v) solution of COH102 in water. The formation of a gel in seconds to hours was scored as "+".
[2]Molecular weight relative to pMMA standards, HPLC on tandem PL gel, molecular sieve columns, in dimethyl formamide solvent at 1.0 ml/min flow rate.

Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention as set forth in the claims which follow. All publications, patents, and patent applications cited in this specification are incorporated herein by reference as if each such publication, patent, or patent application was specifically and individually indicated to be incorporated herein by reference.

We claim:

1. A composition for forming a matrix useful as a high strength medical sealant, wherein said matrix-forming composition comprises:
   a) a first multifunctional synthetic polymer having a core and m functional groups, X;
   b) a multifunctional crosslinker having n functional groups, Y, wherein the sum of m and n is greater than or equal to 5, and X and Y react to form a covalent crosslink Z upon admixture of the first multifunctional synthetic polymer and the multifunctional crosslinker; and
   c) a tensile strength enhancer comprised of a fibrous material selected from the group consisting of polyglycolide, polylactide, polyglycolide-polylactide copolymers, glass wool, plastics, resins, and combinations thereof,
      wherein the high strength medical sealant formed by reaction of the first multifunctional synthetic polymer with the multifunctional crosslinker has at least 10% of the tensile strength of cyanoacrylate.

2. The composition according to claim 1, wherein the multifunctional crosslinker is a second multifunctional synthetic polymer.

3. The composition according to claim 2, wherein at least one of the first or second multifunctional synthetic polymers further comprises a chain extender.

4. The composition according to claim 3, wherein the chain extender is comprised of a biodegradable material.

5. The composition according to claim 4, wherein the chain extender biodegrades at a faster rate in situ than the first and second multifunctional synthetic polymers.

6. The composition according to claim 4, wherein the chain extender is an alpha-hydroxy acid, a poly(lactone), a poly(orthocarbonate) or a poly(phosphoester).

7. The composition according to claim 4, wherein the first and second multifunctional synthetic polymers biodegrade at a faster rate in situ than the chain extender.

8. The composition according to claim 4, wherein the chain extender is enzymatically degradable.

9. The composition according to claim 1, further comprising a rigid nanofiber.

10. The composition according to claim 9, wherein the nanofiber is comprised of a biopolymer.

11. The composition according to claim 10, wherein the biopolymer is selected from the group consisting of methylated collagen, tubulin and keratin.

12. The composition according to claim 11, wherein the biopolymer is methylated collagen.

13. The composition according to claim 1, further comprising an additional compound selected from the group consisting of glycosaminoglycans, proteins, and peptide fragments.

14. The composition according to claim 13, wherein the additional compound is a protein.

15. The composition according to claim 14, wherein the protein is collagen, fibronectin, gelatin, albumin, or peptide fragments thereof.

16. The composition according to claim 15, wherein the protein is collagen.

17. The composition according to claim 16, wherein the collagen is afibrillar, microfibrillar or fibrillar collagen.

18. The composition according to claim 16, wherein the collagen is Type I collagen.

19. The composition according to claim 16, wherein the collagen is Type III collagen.

20. The composition according to claim 16, wherein the collagen is esterified.

21. The composition according to claim 20, wherein the collagen is methylated, ethylated, propylated or benzylated collagen.

22. The composition according to claim 20, wherein the collagen is methylated collagen.

23. The composition according to claim 13, wherein the additional compound is a glycosaminoglycan.

24. The composition according to claim 23, wherein the glycosaminoglycan is selected from the group consisting of hyaluronic acid, chitin, chondroitin sulfate A, B or C, keratin sulfate, keratosulfate and heparin.

25. The composition according to claim 1, further comprising an antibiotic, a growth factor or a hemostatic agent.

26. The composition according to claim 1, wherein m and n are each 4 or greater.

27. The composition according to claim 1, wherein the tensile strength enhancer is selected from the group consisting of polyglycolide, polylactide and copolymers thereof.

28. The composition according to claim 27, wherein the tensile strength enhancer is polyglycolide.

29. The composition according to claim 27, wherein the tensile strength enhancer is polylactide.

30. The composition according to claim 27, wherein the tensile strength enhancer is a polyglycolide-polylactide copolymer.

31. The composition according to claim 30, wherein the polyglycolide-polylactide copolymer has a glycolide-lactide ratio of approximately 90:10.

32. The composition according to claim 1, wherein X is sulfhydryl and Y is a sulfhydryl-reactive group.

33. The composition according to claim 32, wherein the sulfhydryl-reactive group is selected to form a thioether, thioester, imido-thioester, or disulfide bond upon reaction with a sulfhydryl group.

34. The composition according to claim 33, wherein the sulthydryl-reactive group is maleimido, succinimidyl, acrylate, or epoxy.

35. The composition according to claim 1, wherein X is amino and Y is an amino-reactive group.

36. The composition according to claim 35, wherein the amino-reactive group is succinimidyl or acrylate.

37. The composition according to claim 32 or claim 35, further comprising a buffer solution that maintains the composition at an acidic pH effective to prevent reaction between the first multifunctional synthetic polymer and the multifunctional crosslinker.

38. The composition according to claim 37, wherein the acidic pH is in the range of 2 to 4.

39. A method for providing a high strength medical sealant on a surface, comprising:
   providing the composition of claim 1;
   adding a pH-increasing activator to the composition to provide a pH sufficiently high to enable reaction between the first multifunctional synthetic polymer and the multifunctional crosslinking agent; and
   applying the activated composition to the surface.

40. The method of claim 39, wherein the pH-increasing activator is a basic buffer solution.

41. A method for effecting the nonsurgical attachment of a first tissue surface to a second tissue surface, comprising:
   (a) applying the composition of claim 1 to the first tissue surface; and (b) contacting the first tissue surface with the second tissue surface to effect adhesion therebetween.

42. A method for applying a sealing layer to a native tissue surface, comprising applying the composition of claim 1 to the native tissue surface and allowing reaction to occur between the first multifunctional synthetic polymer and the multifunctional crosslinking agent.

43. A method for effecting surgical adhesion, comprising applying the composition of claim 1 to a wound or suture and allowing reaction to occur between the first multifunctional synthetic polymer and the multifunctional crosslinking agent.

44. A method for providing a sealant coating on the surface of a synthetic implant, comprising applying the composition of claim 1 to the surface of the synthetic implant, and allowing reaction to occur between the first multifunctional synthetic polymer and the multifunctional crosslinking agent.

45. A composition for forming a matrix useful as a high strength medical sealant, wherein said matrix-forming composition comprises:
   a) a polyalkylene oxide having n nucleophilic groups, X;
   b) a polyalkylene oxide having n electrophilic groups, Y, wherein the sum of m and n is greater than or equal to 5, and X and Y react to form a covalent crosslink Z upon admixture of a) and b) under crosslinking conditions;
   c) a rigid nanofiber; and
   d) a fibrous tensile strength enhancer, and
      wherein the high strength medical sealant formed by reaction of a) and b) has at least 10% of the tensile strength of cyanoacrylate.

46. The composition according to claim 45, wherein the rigid nanofiber comprises methylated collagen.

47. A biocompatible polymer device for use in treating tissues comprising a collagen sponge or sheet incorporated with a two-part reactive polyethylene glycol powder, wherein said reactive powder further comprises a first polyethylene glycol having multiple nucleophilic groups and a second polyethylene glycol having multiple electrophilic groups, wherein the polyethylene glycol powder remains unreactive until contacted with a high pH buffer.

48. A system for forming a high strength medical sealant, comprising:
   a) a first multifunctional synthetic polymer having a core and m functional groups, X;
   b) a multifunctional crosslinker having n functional groups, Y, wherein X and Y react to form a covalent crosslink Z upon admixture of the first multifunctional synthetic polymer and the multifunctional crosslinker, and further wherein the first multifunctional synthetic polymer and the multifunctional crosslinker are physically separated from each other until reaction therebetween is desired;
   c) a tensile strength enhancer comprised of fibers 5 to 40 microns in diameter and 20 to 5000 microns in length and having a glass transition temperature above 37° C.; and
   d) a rigid nanofiber,
      wherein the high strength medical sealant formed upon reaction of the first multifunctional synthetic polymer and the multifunctional crosslinker has at least 10% of the tensile strength of cyanoacrylate.

49. The system according to claim 48, wherein the multifunctional crosslinker is a second multifunctional synthetic polymer.

50. The system according to claim 49, wherein at least one of the first or second multifunctional synthetic polymers further comprises a chain extender.

51. The system according to claim 50, wherein the chain extender is comprised of a biodegradable material.

52. The system according to claim 51, wherein the chain extender biodegrades at a faster rate in situ than the first and second multifunctional synthetic polymers.

53. The system according to claim 51, wherein the chain extender is an alpha-hydroxy acid, a poly(lactone), a poly(orthocarbonate) or a poly(phosphoester).

54. The system according to claim 51, wherein the first and second multifunctional synthetic polymers biodegrade at a faster rate in situ than the chain extender.

55. The system according to claim 51, wherein the chain extender is enzymatically degradable.

56. The system according to claim 48, further comprising an additional compound selected from the group consisting of glycosaminoglycans, proteins, and peptide fragments.

57. The system of claim 56, wherein the additional compound is a protein.

58. The system according to claim 57, wherein the protein is collagen, fibronectin, gelatin, albumin, or peptide fragments thereof.

59. The system according to claim 58, wherein the protein is collagen.

60. The system according to claim 59, wherein the collagen is afibrillar, microfibrillar or fibrillar collagen.

61. The system according to claim 59, wherein the collagen is Type I collagen.

62. The system according to claim 59, wherein the collagen is Type III collagen.

63. The system according to claim 59, wherein the collagen is esterified.

64. The system according to claim 63, wherein the collagen is methylated, ethylated, propylated or benzylated collagen.

65. The system according to claim 56, wherein the additional compound is a glycosaminoglycan.

66. The system according to claim 65, wherein the glycosaminoglycan is selected from the group consisting of hyaluronic acid, chitin, chondroitin sulfate A, B or C, keratin sulfate, keratosulfate and heparin.

67. The system according to claim 48, wherein X is sulfhydryl and Y is a sulfhydryl-reactive group.

68. The system according to claim 67, wherein the sulfhydryl-reactive group is selected to form a thioether, thioester, imido-thioester, or disulfide bond upon reaction with a sulfhydryl group.

69. The system according to claim 68, wherein the sulfhydryl-reactive group is maleimido, succinimidyl, acrylate, or epoxy.

70. The system according to claim 48, wherein X is amino and Y is an amino-reactive group.

71. The system according to claim 70, wherein the amino-reactive group is succinimidyl or acrylate.

72. The system according to claim 48, wherein at least one of the first multifunctional synthetic polymer and the multifunctional crosslinking agent is in an aqueous solution.

73. The system according to claim 48, wherein the nanofiber is comprised of a biopolymer.

74. The system of claim 73, wherein the biopolymer is selected from the group consisting of methylated collagen, tubulin and keratin.

75. The system of claim 74, wherein the biopolymer is methylated collagen.

76. A method for providing a high strength medical sealant on a surface, comprising:

providing the system of claim 48;

adding a pH-increasing activator to the composition to provide a pH sufficiently high to enable reaction between the first multifunctional synthetic polymer and the multifunctional crosslinking agent; and applying the activated composition to the surface.

77. The method of claim 76, wherein the pH-increasing activator is a basic buffer solution.

78. A method for effecting the nonsurgical attachment of a first tissue surface to a second tissue surface, comprising:

(a) applying the system of claim 48 to the first tissue surface; and (b) contacting the first tissue surface with the second tissue surface to effect adhesion therebetween.

79. A method for applying a sealing layer to a native tissue surface, comprising applying the system of claim 48 the native tissue surface and allowing reaction to occur between the first multifunctional synthetic polymer and the multifunctional crosslinking agent.

80. A method for effecting surgical adhesion, comprising applying the system of claim 48 to a wound or suture and allowing reaction to occur between the first multifunctional synthetic polymer and the multifunctional crosslinking agent.

81. A method for providing a sealant coating on the surface of a synthetic implant, comprising applying the system of claim 48 to the surface of the synthetic implant, and allowing reaction to occur between the first multifunctional synthetic polymer and the multifunctional crosslinking agent.

* * * * *

UNITED STATES PATENT AND TRADEMARK OFFICE
CERTIFICATE OF CORRECTION

PATENT NO.   : 6,495,127 B1
DATED        : December 17, 2002
INVENTOR(S)  : Donald G. Wallace et al.

It is certified that error appears in the above-identified patent and that said Letters Patent is hereby corrected as shown below:

Column 39,
Line 49, after "wherein" please insert -- the sum of m and n is greater than or equal to 5, and --.

Column 40,
Line 2, please delete "multifimctional" and replace with -- multifunctional --.

Column 41,
Line 17, after "48" please insert -- to --.

Column 42,
Line 3, please delete "fimctional" and replace with -- functional --.

Signed and Sealed this

Twenty-sixth Day of August, 2003

JAMES E. ROGAN
*Director of the United States Patent and Trademark Office*